(12) United States Patent
Hauck

(10) Patent No.: US 11,219,535 B1
(45) Date of Patent: Jan. 11, 2022

(54) INTERBODY FUSION SYSTEM

(71) Applicant: Brian Albert Hauck, Windsor, CA (US)

(72) Inventor: Brian Albert Hauck, Windsor, CA (US)

(*) Notice: Subject to any disclaimer, the term of this patent is extended or adjusted under 35 U.S.C. 154(b) by 169 days.

(21) Appl. No.: 16/666,303

(22) Filed: Oct. 28, 2019

Related U.S. Application Data

(60) Provisional application No. 62/751,799, filed on Oct. 29, 2018.

(51) Int. Cl.
*A61F 2/44* (2006.01)
*A61F 2/46* (2006.01)
*A61F 2/30* (2006.01)

(52) U.S. Cl.
CPC .......... *A61F 2/4611* (2013.01); *A61F 2/3094* (2013.01); *A61F 2/4455* (2013.01); *A61F 2002/30092* (2013.01); *A61F 2002/30131* (2013.01)

(58) Field of Classification Search
CPC .......... A61F 2/44; A61F 2/442; A61F 2/4455; A61F 2/446; A61F 2/4465; A61F 2/447; A61F 2002/443; A61F 2002/444; A61F 2002/448; A61F 2002/4485
See application file for complete search history.

(56) References Cited

U.S. PATENT DOCUMENTS 9,592,132 B2 * 3/2017 Hauck .................. A61F 2/4455
9,913,728 B2 * 3/2018 Ainsworth ............. A61F 2/447
2007/0067035 A1 * 3/2007 Falahee ................. A61F 2/4455 623/17.11
2008/0125865 A1 * 5/2008 Abdelgany ........... A61F 2/4425 623/17.16
2008/0249628 A1 * 10/2008 Altarac ................. A61F 2/4611 623/17.16
2008/0312743 A1 * 12/2008 Vila ...................... A61F 2/4465 623/17.16
2011/0009969 A1 * 1/2011 Puno .................... A61F 2/4684 623/17.12
2012/0071980 A1 * 3/2012 Purcell ................. A61F 2/4455 623/17.16
2014/0277481 A1 * 9/2014 Lee ...................... A61F 2/4455 623/17.16
2014/0277498 A1 * 9/2014 Ainsworth ........... A61F 2/4455 623/17.16

(Continued)

*Primary Examiner* — Eric S Gibson
(74) *Attorney, Agent, or Firm* — Robert Crownover

(57) ABSTRACT

A method and apparatus can include: a delivery tool having an insertion mandrel; an implant having a distal segment coupled to a proximal segment, the proximal segment having a proximal segment upper and a proximal segment lower, the distal segment having a distal segment upper and a distal segment lower, the implant including: a straight configuration based on the insertion mandrel being extended through the proximal segment and the distal segment, and a curved configuration based on the insertion mandrel being retracted from the distal segment; and an expansion mandrel configured for insertion into the implant, the implant including an expanded configuration based on the expansion mandrel being inserted between the proximal segment upper and the proximal segment lower, and being inserted between the distal segment upper and the distal segment lower.

20 Claims, 16 Drawing Sheets

(56) References Cited

U.S. PATENT DOCUMENTS

2016/0074174 A1\* 3/2016 Halverson ............. A61F 2/4455
  623/17.11
2016/0199195 A1\* 7/2016 Hauck ................... A61F 2/4455
  623/17.16

\* cited by examiner

US 11,219,535 B1

INTERBODY FUSION SYSTEM

CROSS-REFERENCE TO RELATED APPLICATION(S)

This claims priority benefit to all common subject matter of U.S. Provisional Patent Application No. 62/751,799 filed Oct. 29, 2018. The content of this applications is incorporated herein by reference in its entirety.

TECHNICAL FIELD

This disclosure relates to interbody fusion systems, more particularly to segmented expandable fusion systems.

BACKGROUND

Spinal fusion is sometimes necessary for patients having lumbar degenerative disc disease. It has been estimated that at least thirty percent of people aged thirty to fifty will have some degree of disc space degeneration, although not all will have pain or ever be diagnosed formally with degenerative disc disease. After a patient reaches sixty, it is more normal than not to have some level of disc degeneration.

A twisting injury often starts degenerative disc diseases, but it can also be initiated by everyday wear and tear on the spine. Lower back pain is the most common symptom of a compromised disc emblematic of degenerative disc diseases. For most patients with lumbar degenerative disc disease, the pain is for the most part tolerable and low-grade, but continuous with occasional flaring of intense pain.

Pain can be simply centered on the lower back, or it can radiate to the hips and legs. It can get worse by sitting, or it can be intensified by twisting, lifting, or bending. For some, the pain from the disease decreases over time, since a fully degenerated disc has no pain-causing inflammatory proteins, and the disc usually collapses into a stable position-eliminating the micro-motion that often generates the pain.

Stabilization of vertebrae relative to each other, by implanting inter-body fusion devices, is a well-accepted surgical technique and has increasingly been used to correct for degenerative disc disease. The implantation of internal fusion devices can often be traumatic. If insufficient stabilization or incorrect anatomical alignment occurs, then revision surgery or on-going pain may be experienced by the patient.

Many variations of this basic surgical technique exist but often require considerable time and effort for successful implant placement. This is frequently due to the fact that such systems typically require both excessive surgical tissue dissection and mechanical vertebral distraction such that the various stabilization components of the system can be successfully positioned in a patient's intervertebral space.

In addition, dimensional constraints typically imposed by access considerations are often in conflict with the desire to place the largest implant possible having an effective anatomical shape to support the loads transmitted across the vertebral endplates. Specifically, the larger and more curved the implant inserted, the greater the amount of resulting tissue damage both in the intervertebral space, and in the surrounding tissues. Accordingly, the need for spinal fusion devices with increased expansion, articulation, controllability, and precision has arisen.

Solutions have been sought but prior developments have not taught or suggested any complete solutions, and solutions to these problems have eluded those skilled in the art. Thus, a considerable need still remains.

SUMMARY

A fusion system and methods, providing significant expansion, articulation, controllability, and precision are disclosed. The fusion system and methods can include: a delivery tool having an insertion mandrel; an implant having a distal segment coupled to a proximal segment, the proximal segment having a proximal segment upper and a proximal segment lower, the distal segment having a distal segment upper and a distal segment lower, the implant including: a straight configuration based on the insertion mandrel being extended through the proximal segment and the distal segment, and a curved configuration based on the insertion mandrel being retracted from the distal segment; and an expansion mandrel configured for insertion into the implant, the implant including an expanded configuration based on the expansion mandrel being inserted between the proximal segment upper and the proximal segment lower, and being inserted between the distal segment upper and the distal segment lower.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The fusion system is illustrated in the figures of the accompanying drawings which are meant to be exemplary and not limiting, in which like reference numerals are intended to refer to like components, and in which:

FIG. 17 13 is a cross-sectional isometric view of the fusion system of FIG. 16 in a filled state.

FIG. 18 12 is an isometric view of Section C of FIG. 16.

DETAILED DESCRIPTION

Figure 1:
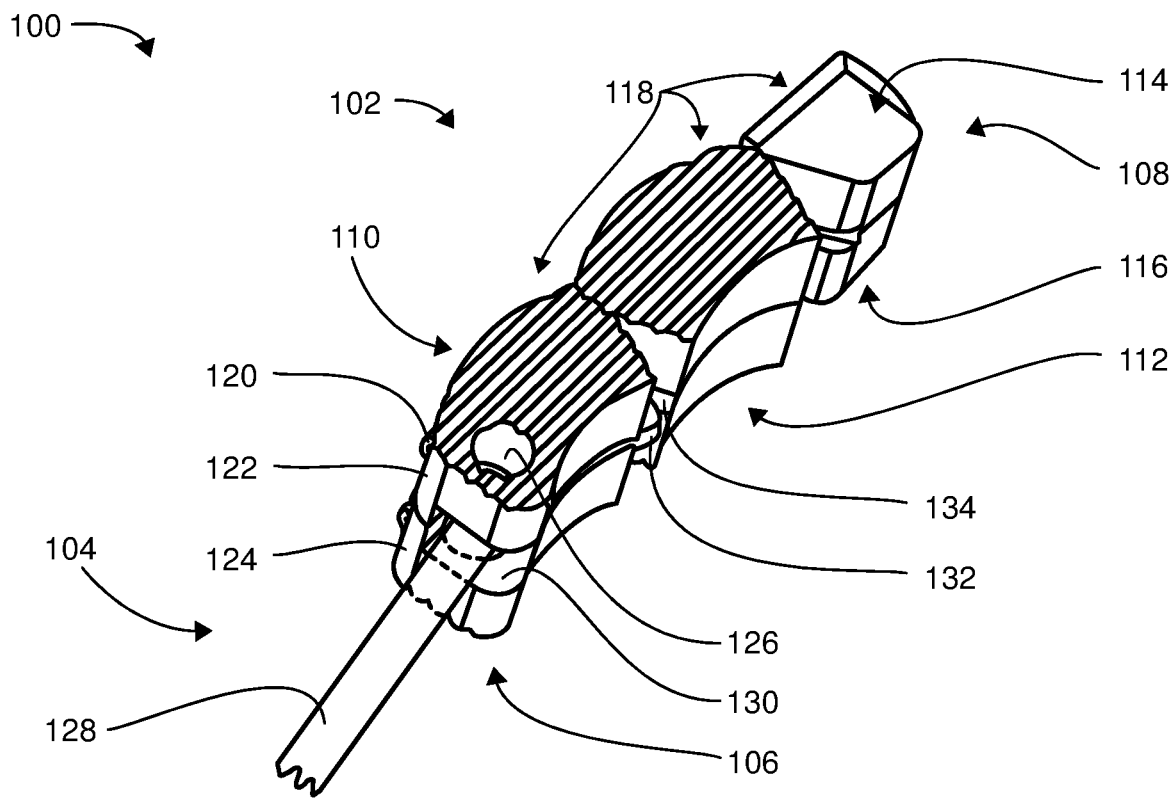
FIG. 1 is an isometric view of the fusion system in a first embodiment and in a straight configuration.

In the following description, reference is made to the accompanying drawings that form a part hereof, and in which are shown by way of illustration, embodiments in which the fusion system may be practiced. It is to be understood that other embodiments may be utilized and structural changes may be made without departing from the scope of the fusion system.

When features, aspects, or embodiments of the fusion system are described in terms of steps of a process, an operation, a control flow, or a flow chart, it is to be understood that the steps can be combined, performed in a different order, deleted, or include additional steps without departing from the fusion system as described herein.

The fusion system is described in sufficient detail to enable those skilled in the art to make and use the fusion system and provide numerous specific details to give a thorough understanding of the fusion system; however, it will be apparent that the fusion system may be practiced without these specific details.

In order to avoid obscuring the fusion system, some well-known system configurations and descriptions are not disclosed in detail. Likewise, the drawings showing embodiments of the system are semi-diagrammatic and not to scale and, particularly, some of the dimensions are for the clarity of presentation and are shown greatly exaggerated in the drawing FIGs.

Referring now to FIG. 1, therein is shown an isometric view of the fusion system 100 in a first embodiment and in a straight configuration. The fusion system 100 is depicted having an implant 102 pivotally attachable to a delivery tool 104.

The implant 102 is contemplated to be an expandable multi-segment interbody fusion implant for insertion into vertebral disk space. The implant 102 can pivot at the interface between the delivery tool 104 and the implant 102.

For the purposes of this disclosure, the implant 102 will be described with regard to a proximal end 106, a distal end 108, an outer curved surface 110, an inner curved surface 112, a top surface 114, and a bottom surface 116.

The proximal end 106 is the end of the implant 102 closest to and coupled with the delivery tool 104. The proximal end 106 will also be closer to an operator or user during implantation of the implant 102.

The distal end 108 is the end of the implant 102 opposite from the proximal end 106 when the implant 102 is in the straight configuration. The outer curved surface 110 and the inner curved surface 112 can each extend between the top surface 114 and the bottom surface 116 of the implant 102.

The outer curved surface 110 can provide a larger area, when the implant 102 is in the curved configuration, than the inner curved surface 112. The implant 102 is shown having three segments 118. The segments 118 can be made of a bio-compatible material.

For ease of description, the segments 118 can be referred to as the proximal segment, the distal segment, and the middle segment. However, it is to be understood that the disclosure is not limited to a specific number of segments unless otherwise claimed.

The segments 118 can be coupled together with a flexible guide 120. The flexible guide 120 can extend through the segments 118 and can have a pre-defined curved shape.

The flexible guide 120 can be a flexible wire, ribbon, or cable. It is contemplated that the flexible guide 120 may be made from a shape memory or super elastic material. These can include both shape memory alloys, such as nitinol, and shape memory polymers. The shape memory alloys and polymers should be understood to have the ability to return from a deformed state to an original and permanent shape induced by an external stimulus, such as a temperature or pressure change.

Figure 5:
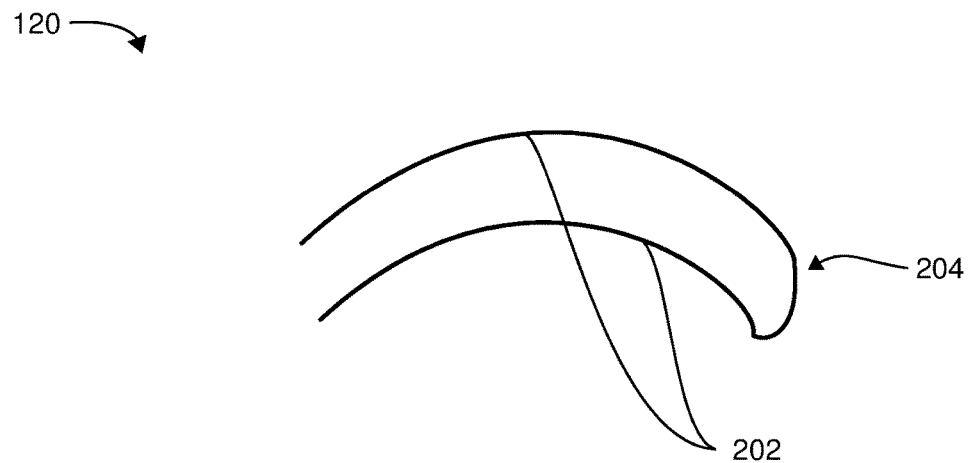
FIG. 5 is a top view of the flexible guide of FIG. 4.

The flexible guide 120 can be made from a bio-compatible material such as stainless steel. Further, the flexible guide 120 can have a pre-defined curved shape, as shown in FIG. 5, below.

Each of the segments 118 can include a segment upper 122 and a segment lower 124. The flexible guide 120 can extend continuously through the segment upper 122 and the segment lower 124 of each of the segments 118 and can wrap around the distal end 108.

The implant 102 can be expanded by moving the segment upper 122 and the segment lower 124 away from each other. When this expansion is performed during implantation of the fusion system 100, the segment upper 122 and the segment lower 124 will expand in the spine's longitudinal direction.

As depicted in FIG. 1, the implant 102 is in a non-expanded configuration with the segment upper 122 and the segment lower 124 in direct contact with one another. The segment upper 122 and the segment lower 124 can be expanded with an expansion mandrel and held to one another with flexible connectors, which are depicted, for example, in the expanded configuration of FIG. 7.

The proximal segment is shown having a pivoting attachment joint 126. The attachment joint 126 is pivotally coupled to the delivery tool 104 containing an insertion mandrel 128. The insertion mandrel 128 can have a non-circular cross-section in order to transmit torque between the implant 102 and the delivery tool 104.

The insertion mandrel 128 can extend through the segments 118 of the implant 102 to impart the straight configuration to the segments 118 by temporarily deforming the flexible guide 120. As the insertion mandrel 128 is removed from the segments 118, the flexible guide 120 will return to the pre-defined curved shape and the segments 118 will enter the curved configuration of FIG. 4, for example.

The delivery tool 104 can pivot about the attachment joint 126 and can pivot towards the inner curved surface 112 of the segments 118 by pivoting through a pivot recess 130. The pivot recess 130 can provide space for the delivery tool 104 to move between the segment upper 122 and the segment lower 124 near the attachment joint 126 of the proximal segment.

The proximal segment and the middle segment are shown having an alignment protrusion 132 for mating with an alignment recess 134 within the adjacent middle segment or distal segment. The alignment protrusions 132 together with the alignment recess 134 can provide additional mechanical rigidity when the fusion system is in the curved configuration.

Figure 2:
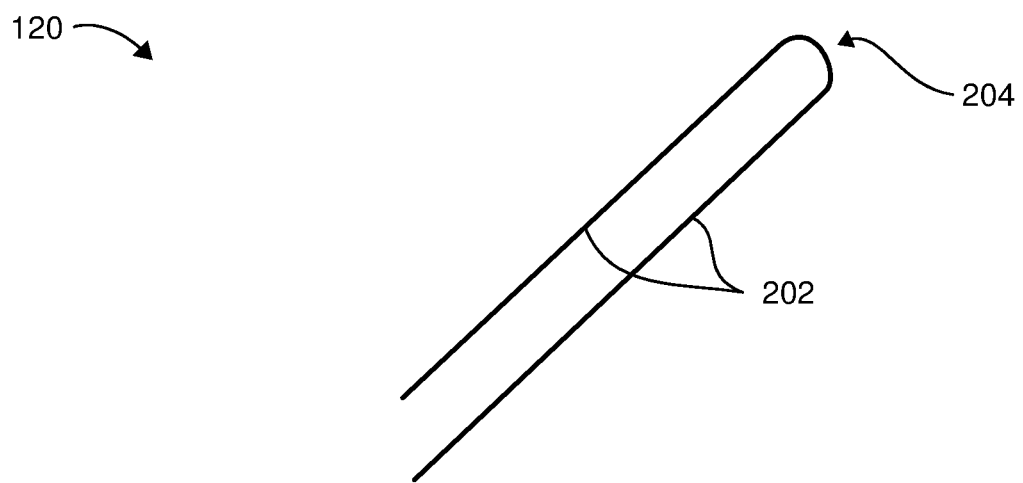
FIG. 2 is a top view of the flexible guide of FIG. 1.

Referring now to FIG. 2, therein is shown a top view of the flexible guide 120 of FIG. 1. The flexible guide 120 is shown in a temporary deformed state, which is substantially straight.

The flexible guide 120 is depicted having two extensions 202, which are shown as long parallel portions of the flexible guide 120. The extensions 202 can extend through the segments 118 of FIG. 1.

The flexible guide 120 is further shown including a coupling end 204. The coupling end 204 can couple the two extensions 202, connecting them at the distal end 108 of the implant 102 of FIG. 1.

The flexible guide 120 is contemplated to extend through both the segment upper 122 of FIG. 1 and the segment lower 124 of FIG. 1. Utilizing the flexible guide 120 within both the segment upper 122 and the segment lower 124 increases mechanical rigidity during implantation.

The flexible guide 120 can be a flexible wire, ribbon, or cable. It is contemplated that the flexible guide 120 may be made from a shape memory or super elastic material. These can include both shape memory alloys, such as nitinol, and shape memory polymers. The shape memory alloys and polymers should be understood to have the ability to return from a deformed state to an original or pre-defined shape induced by an external stimulus, such as a temperature or pressure change. The flexible guide 120 can be made from a bio-compatible material such as stainless steel.

Figure 3:
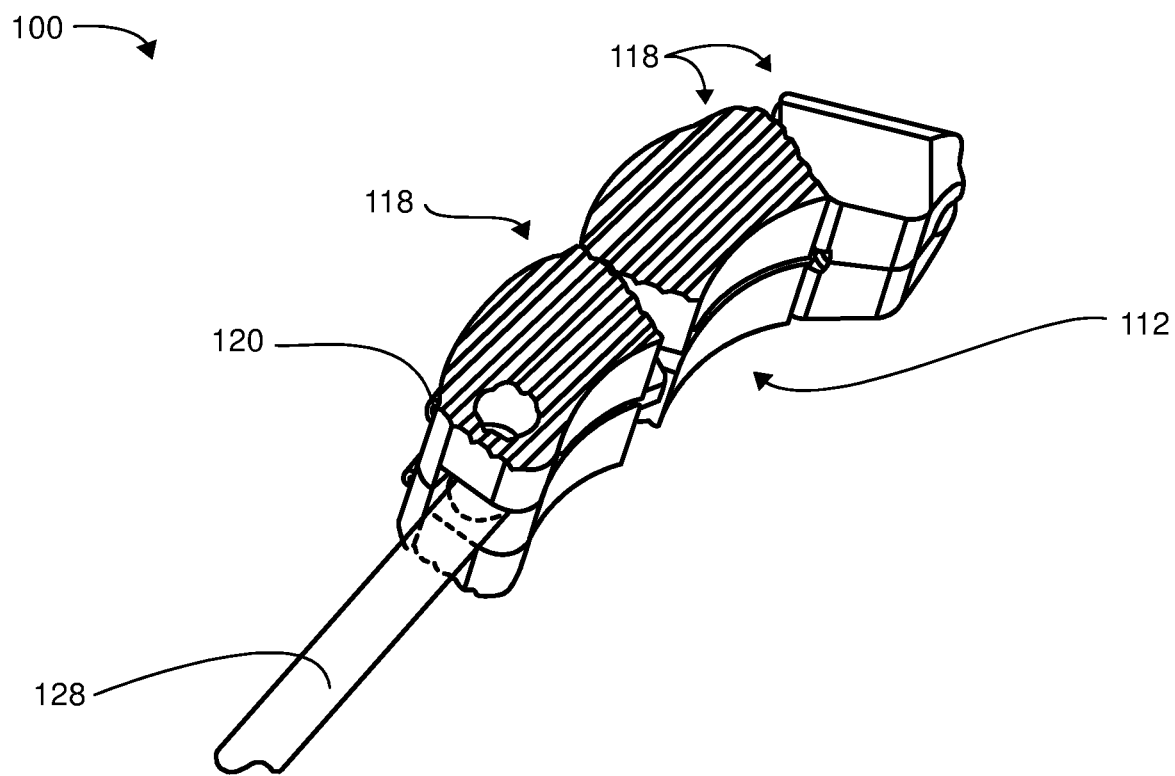
FIG. 3 is an isometric view of the fusion system of FIG. 1 in a semi-straight configuration.

Referring now to FIG. 3, therein is shown an isometric view of the fusion system 100 of FIG. 1 in a semi-straight configuration. The insertion mandrel 128 can be seen removed from within the distal segment.

Without the insertion mandrel 128 extended entirely through the segments 118, the distal segment has rotated toward the inner curved surface 112 of the middle segment. That is, the flexible guide 120 of FIG. 1, between the middle segment and the distal segment, returns to its pre-defined curved shape as the insertion mandrel 128 is removed from within the distal segment.

Figure 4:
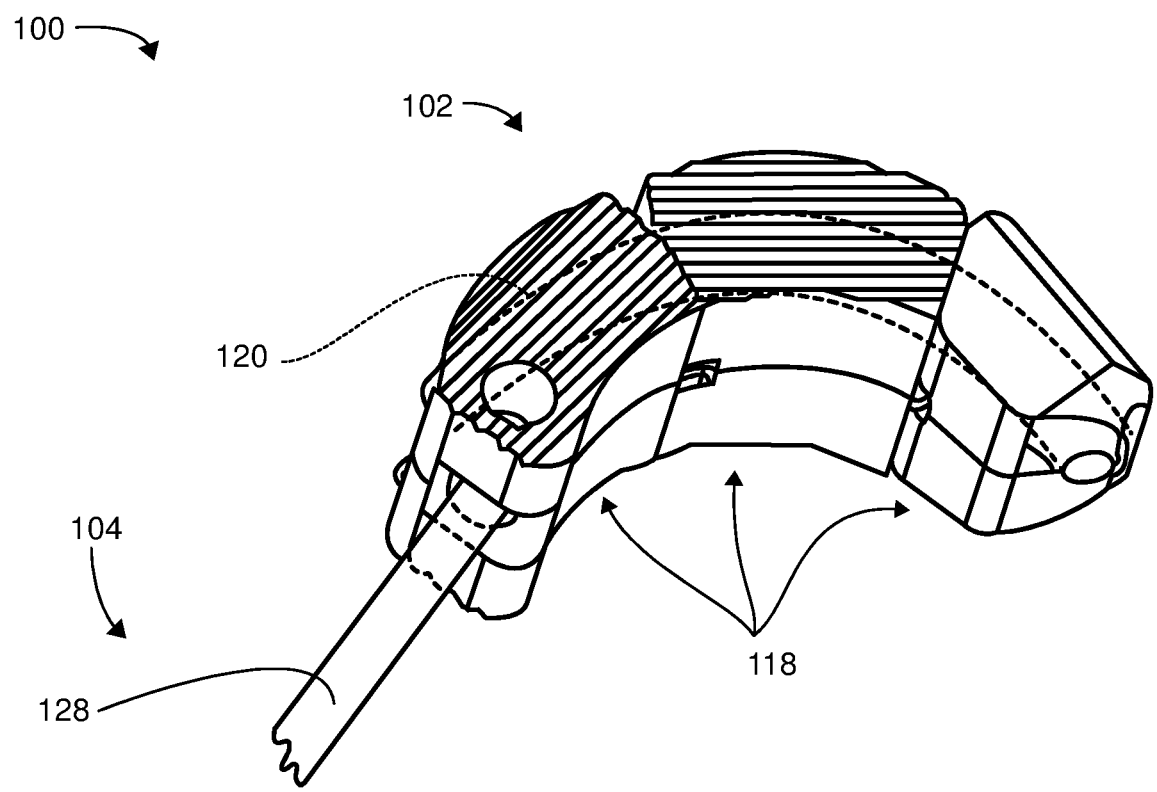
FIG. 4 is an isometric view of the fusion system of FIG. 1 in a curved configuration.

Referring now to FIG. 4, therein is shown an isometric view of the fusion system 100 of FIG. 1 in a curved configuration. The implant 102 is shown having the insertion mandrel 128 fully withdrawn or retracted from the distal segment and from the middle segment of the implant 102 leaving only the proximal segment having the insertion mandrel 128 contained therein.

As a result of the insertion mandrel 128 being removed from the distal and middle segments, the segments 118 have now formed the curved configuration. The curved configuration results from the flexible guide 120 returning to its pre-defined curved shape once the insertion mandrel 128 is removed from the segments 118.

The flexible guide 120 is depicted extending through the segments 118 in a curved shape. The insertion mandrel 128 of the delivery tool 104 can still be used to push, pull, lever, or twist the implant 102 when the implant 102 is in the curved configuration of FIG. 4, the semi-curved configuration of FIG. 3, or the straight configuration of FIG. 1.

Referring now to FIG. 5, therein is shown a top view of the flexible guide 120 of FIG. 4. The flexible guide 120 is shown in a pre-defined resting state, which is substantially curved.

The flexible guide 120 is depicted having the two extensions 202 as long parallel portions of the flexible guide 120. The extensions 202 can extend through the segments 118 of FIG. 1.

The flexible guide 120 is further shown including a coupling end 204. The coupling end 204 can couple the two extensions 202, connecting them at the distal end 108 of the implant 102 of FIG.

The flexible guide 120 is contemplated to extend through both the segment upper 122 of FIG. 1 and the segment lower 124 of FIG. 1. Utilizing the flexible guide 120 within both the segment upper 122 and the segment lower 124 increases mechanical rigidity during implantation.

The flexible guide 120 can be a flexible wire, ribbon, or cable. It is contemplated that the flexible guide 120 may be made from a shape memory or super elastic material. These can include both shape memory alloys, such as nitinol, and shape memory polymers. The shape memory alloys and polymers should be understood to have the ability to return from a deformed state to an original or pre-defined shape induced by an external stimulus, such as a temperature or pressure change. The flexible guide 120 can be made from a bio-compatible material such as stainless steel.

Figure 6:
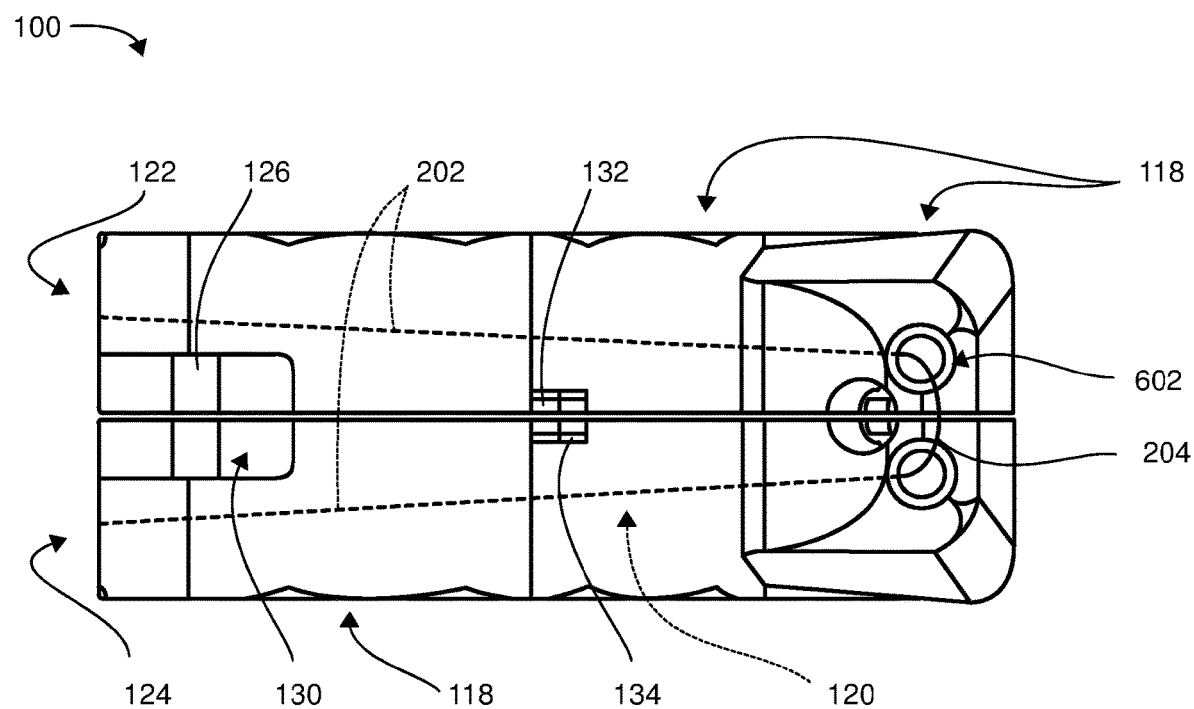
FIG. 6 is a side view of the fusion system of FIG. 3.

Referring now to FIG. 6, therein is shown a side view of the fusion system 100 of FIG. 3. The flexible guide 120 is shown extended through the segments 118.

Specifically, the flexible guide 120 is extended through the segment uppers 122 of the proximal, middle, and distal segments. The flexible guide 120 is further extended through the segment lowers 124 of the proximal, middle, and distal segments.

The flexible guide 120 can extend through guide channels 602 within the segment uppers 122 and the segment lowers 124 of each of the segments 118. The coupling end 204 is shown positioned outside of the distal segment and can couple both extensions 202 of the flexible guide 120.

The attachment joint 126 and pivot recess 130 are shown within the segment upper 122 and the segment lower 124 of the proximal segment. The attachment joint 126 and pivot recess 130 can provide space for the insertion mandrel 128 of FIG. 1 to pivot between the segment upper 122 and the segment lower 124.

The proximal segment is shown with the alignment protrusion 132 mated with the alignment recess 134 within the middle segment. The alignment protrusions 132 together with the alignment recess 134 can provide additional mechanical rigidity when the fusion system is in the curved configuration.

Figure 7:
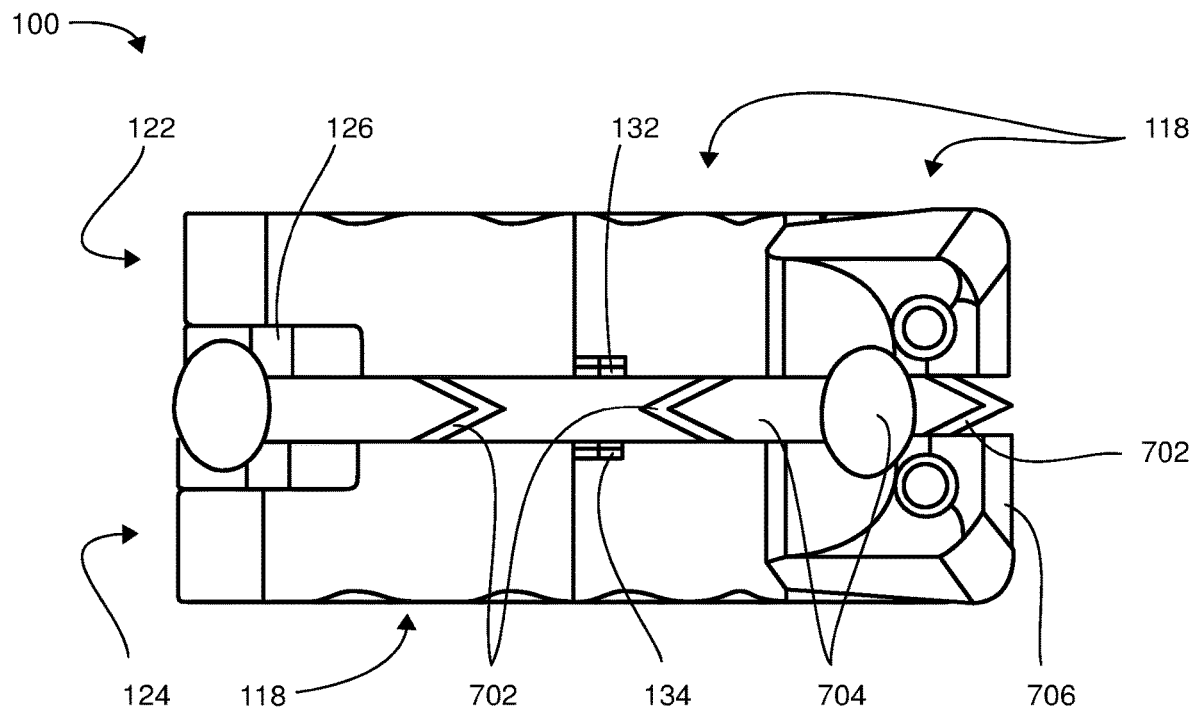
FIG. 7 is a side view of the fusion system of FIG. 1 in an expanded configuration.

Referring now to FIG. 7, therein is shown a side view of the fusion system 100 of FIG. 6 in an expanded configuration. Each of the segments 118 are depicted having the segment uppers 122 extended away from the segment lowers 124. When this expansion is performed during implantation of the fusion system 100, the segment upper 122 and the segment lower 124 will expand in the spine's longitudinal direction.

The segment uppers 122 and the segment lowers 124 are coupled to one another with flexible connections 702 providing resistance to expansion between the segment uppers 122 and the segment lowers 124 for maintaining the implant 102 of FIG. 1 in an unexpanded configuration. The flexible connections 702 can be formed integrally with the segments 118 or can be coupled to the segments 118 during manufacture.

The flexible connections 702 can be made of a shape memory or super elastic material. These can include both shape memory alloys, such as nitinol, and shape memory polymers. The flexible connections 702 can also be made from a bio-compatible material such as stainless steel.

The segment upper 122 and the segment lower 124 can be expanded utilizing an expansion mandrel 704. The expansion mandrel 704 is contemplated to have a cross-sectional measurement larger than the insertion mandrel 128 of FIG. 1.

The expansion mandrel 704 can be flexible, allowing the expansion mandrel 704 to be inserted between the segments 118 while the segments 118 are in the curved configuration. It is contemplated that multiple expansion mandrels 704 can be inserted to allow for incrementally greater expansions between the segment uppers 122 and the segment lowers 124. The segments 118 and expansion mandrel 704 can be made from a bio-compatible material.

The segments 118 are further depicted with the attachment joint 126, formed within the segment upper 122 and the segment lower 124 of the proximal segment, being extended away from one another in the expanded configuration. Further, the alignment protrusion 132 mated with the alignment recess 134 within the middle segment is shown mated within both the segment upper 122 and the segment lower 124.

The segments 118 are further depicted including biologics 706. The biologics 706 can be inserted into the expansion mandrel inner cavity 1204 of FIG. 12 after the expansion mandrel 704 is inserted into and expands the segments 118 allowing the biologics 706 to spread around the segments 118. The biologics 706 can be a bone graft material such as autograft, allograft, other osteoconductive material, or other bone growth material.

Figure 8:
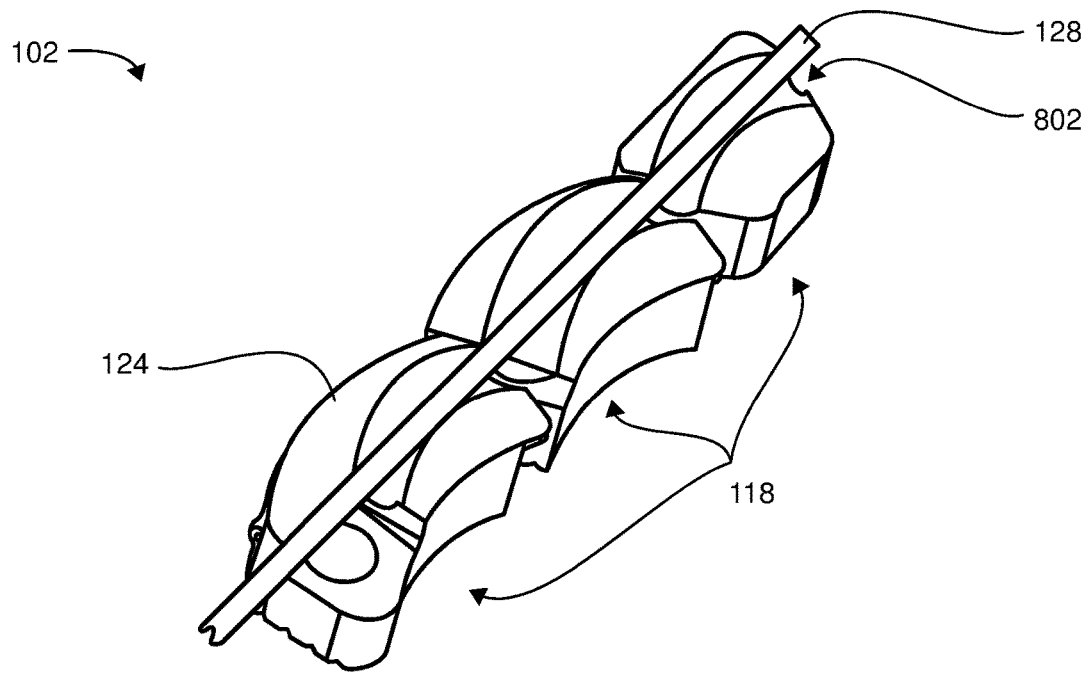
FIG. 8 is a cross-sectional isometric view of the fusion system of FIG. 1 in the straight configuration.

Referring now to FIG. 8, therein is shown a cross-sectional isometric view of the fusion system 100 of FIG. 1 in the straight configuration. The implant 102 is shown having an inner lumen 802 extending through the segment uppers 122 of FIG. 1 and the segment lowers 124 of each of the segments 118. The insertion mandrel 128 is shown extended into and through the inner lumen 802, aligning the segments 118, and forcing the segments 118 into the straight configuration.

Figure 9:
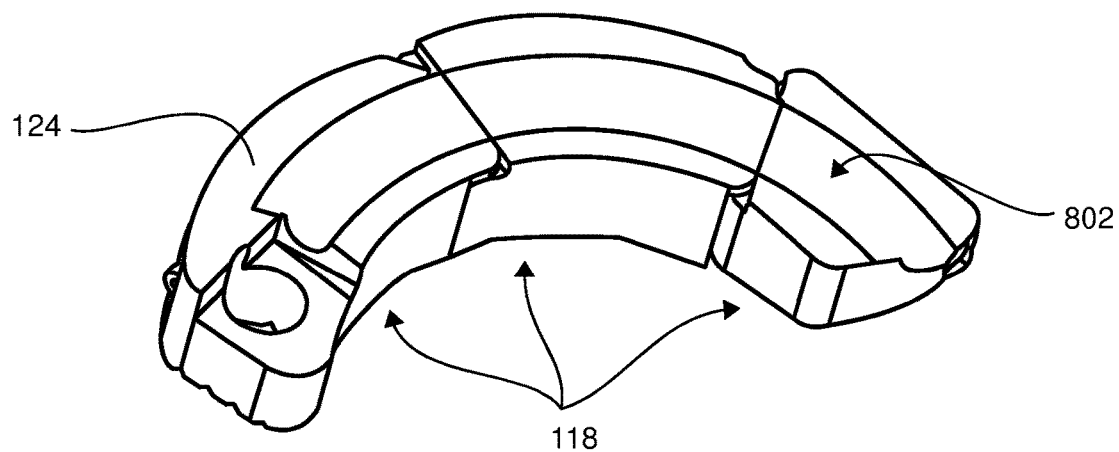
FIG. 9 is a cross-sectional isometric view of the fusion system of FIG. 8 in the curved configuration.

Referring now to FIG. 9, therein is shown a cross-sectional isometric view of the fusion system 100 of FIG. 8 in the curved configuration. The segment lowers 124 of the implant 102 are depicted without the insertion mandrel 128 of FIG. 1 extended through the inner lumen 802.

As will be appreciated, once the insertion mandrel 128 is removed from the segments 118, the segments 118 will return to the curved configuration due to the flexible guide 120 of FIG. 1 returning to its pre-defined curved state.

Figure 10:
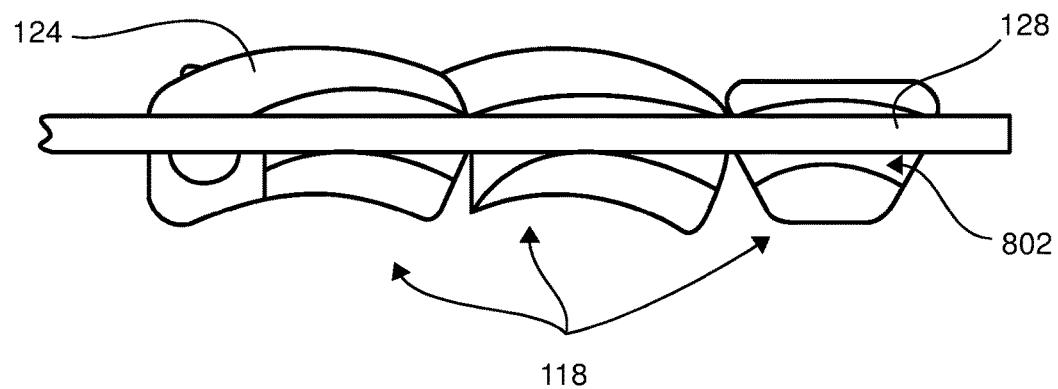
FIG. 10 is a top side cross-sectional view of FIG. 8.

Referring now to FIG. 10, therein is shown a top side cross-sectional view of FIG. 8. The implant 102 is shown having the inner lumen 802.

The inner lumen 802 can extend through the segment uppers 122 of FIG. 1 and the segment lowers 124 of each of the segments 118. The insertion mandrel 128 is shown extended into and through the inner lumen 802, aligning the segments 118, and forcing the segments 118 into the straight configuration.

Figure 11:
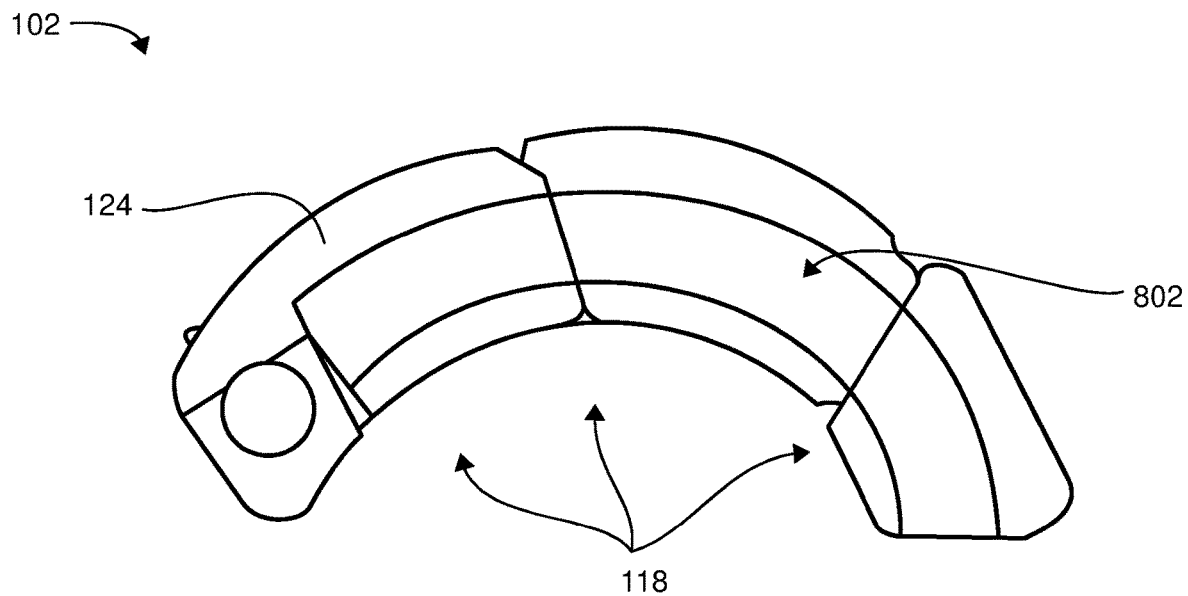
FIG. 11 is a top side cross-sectional view of FIG. 9.

Referring now to FIG. 11, therein is shown a top side cross-sectional view of FIG. 9. The segment lowers 124 of the implant 102 are depicted without the insertion mandrel 128 of FIG. 1 extended through the inner lumen 802.

As will be appreciated, once the insertion mandrel 128 is removed from the segments 118, the segments 118 will return to the curved configuration due to the flexible guide 120 of FIG. 1 returning to its pre-defined curved state.

Figure 12:
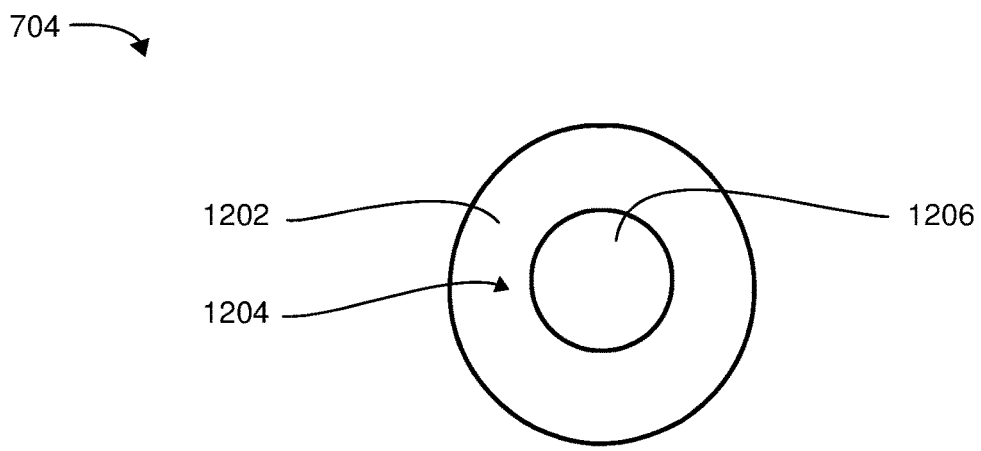
FIG. 12 is a side view of the expansion mandrel of FIG. 7.

Referring now to FIG. 12, therein is shown a side view of the expansion mandrel 704 of FIG. 7. The expansion mandrel 704 is shown having a round expansion mandrel body 1202 surrounding an expansion mandrel inner cavity 1204.

The expansion mandrel inner cavity 1204 can provide space for the expansion mandrel body 1202 to deform during insertion. The expansion mandrel inner cavity 1204 can further provide a channel for delivering biologics 1206 into the segments 118 of FIG. 1 and as is shown in FIG. 7. The expansion mandrel 704 can have a constant cross-section along its length.

Figure 13:
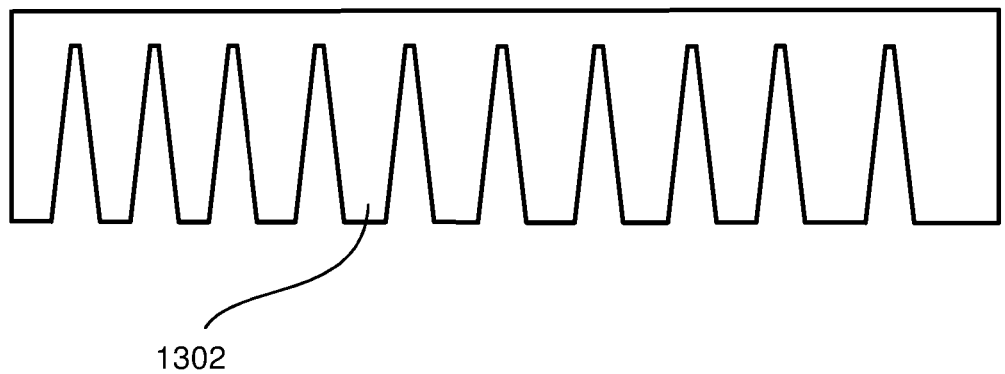
FIG. 13 is a side view of the expansion mandrel of FIG. 12 in a straight configuration.

Referring now to FIG. 13, therein is shown a side view of the expansion mandrel 704 of FIG. 12 in a straight configuration. The expansion mandrel 704 is depicted having wedges 1302. The wedges 1302 can be open when the expansion mandrel 704 is in a straight configuration.

Figure 14:
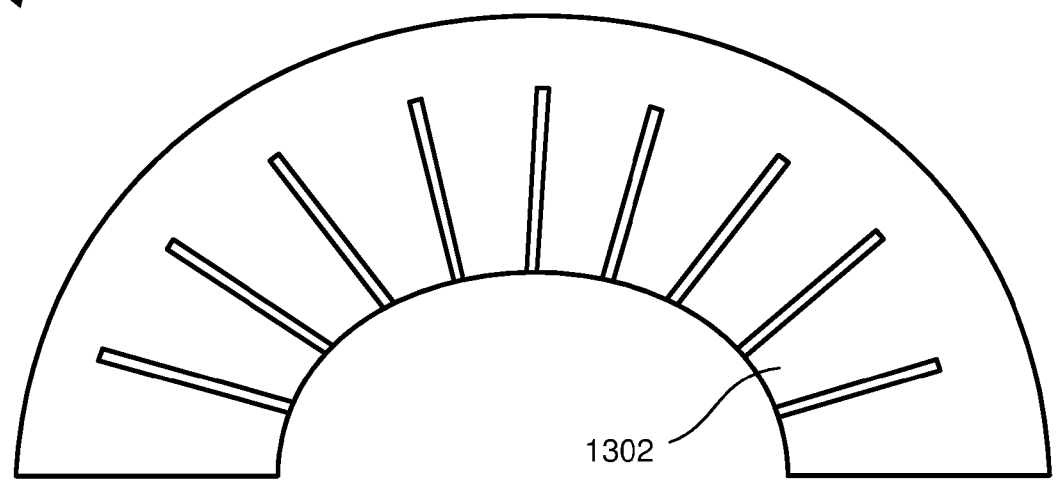
FIG. 14 is a side view of the expansion mandrel of FIG. 12 in a curved configuration.

Referring now to FIG. 14, therein is shown a side view of the expansion mandrel 704 of FIG. 12 in a curved configuration. The expansion mandrel 704 is depicted having the wedges 1302, however, the wedges are closed together in the curved configuration of the expansion mandrel 704.

Figure 15:
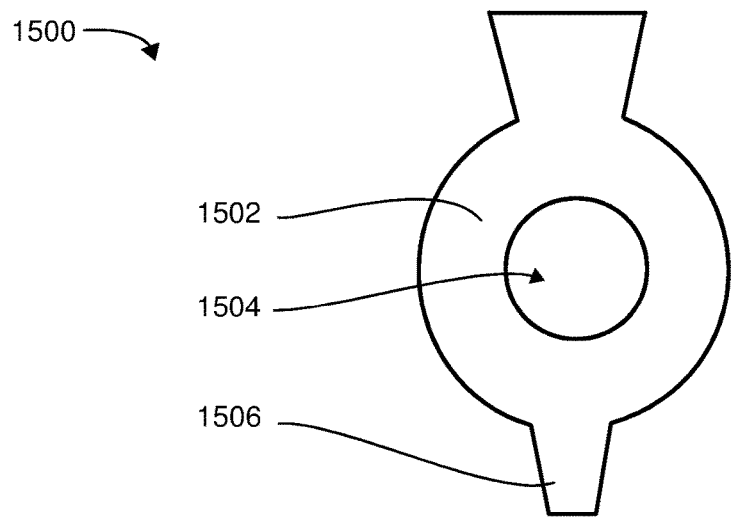
FIG. 15 is an expansion mandrel in a second embodiment.

Referring now to FIG. 15 is an expansion mandrel 1500 in a second embodiment. The expansion mandrel 704 is shown having a round expansion mandrel body 1502 surrounding an expansion mandrel inner cavity 1504.

The expansion mandrel inner cavity 1504 can provide space for the expansion mandrel body 1502 to deform during insertion into the implant 102 of FIG. 1. The expansion mandrel inner cavity 1504 can further provide a channel for delivering biologics into the implant 102. The expansion mandrel 704 can have a constant cross-section along its length.

The expansion mandrel body 1502 can further include mandrel extensions 1506 extending from the surface thereof. Each of the mandrel extensions 1506 can have non-parallel surfaces.

The non-parallel surfaces of the mandrel extensions 1506 can enable a lordosis adjustment of the implant by expanding the implant 102 near the outer curved surface 110 of FIG. 1 more than the implant 102 near the inner curved surface 112 of FIG. 1, for example. That is, the larger mandrel extensions 1506 can correspond to a larger expansion of the implant 102, and when the mandrel extensions 1506 are different sizes, the expansion of the implant 102 will vary based on the size of the mandrel extensions 1506.

Figure 16:
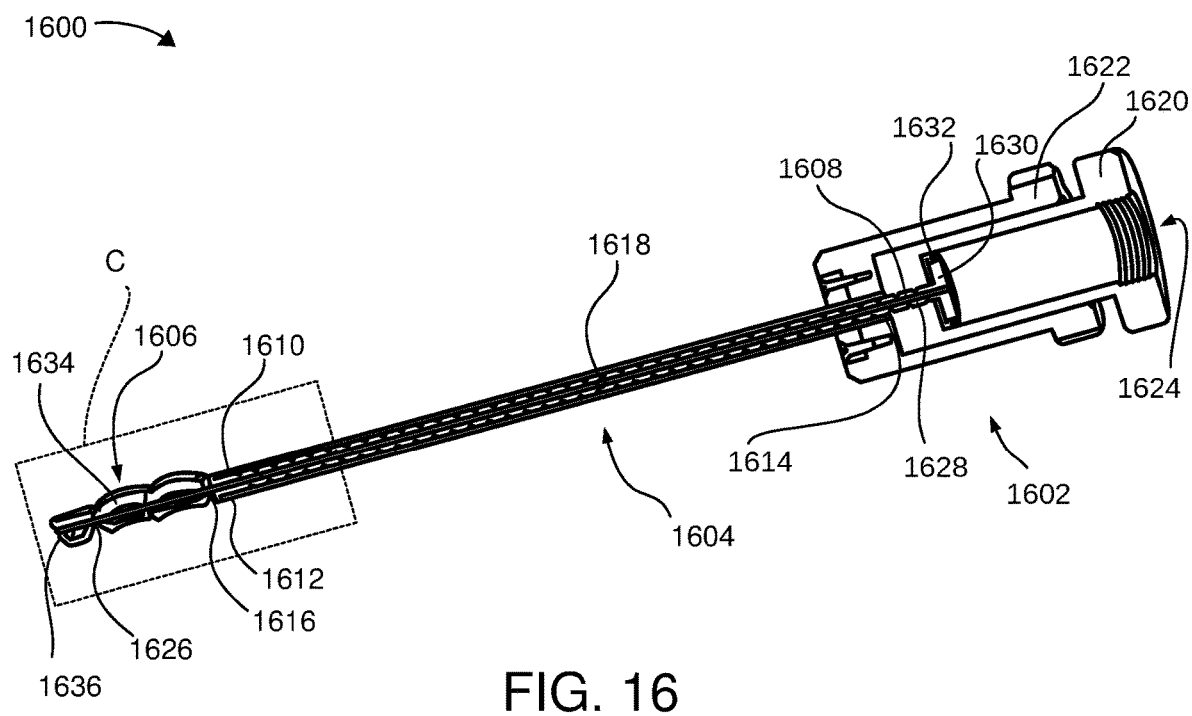
FIG. 16 is a cross-sectional isometric view of the fusion system in a second embodiment and in an empty state.

Referring now to FIG. 16, therein is shown a cross-sectional isometric view of the fusion system 1600 in a second embodiment and in an empty state. The fusion system 1600 is shown with the delivery tool, of the fusion system, in greater detail. For descriptive clarity, the delivery tool is described in detail with regard to FIG. 16 but is to be understood, for the purposes of this application, as depicted and implemented with the other embodiments of this disclosure except where specifically and alternately described; however the delivery tool and its elements are not to be read into the claims unless explicitly recited.

The delivery tool can include a handle 1602 and a shaft 1604. The fusion system 1600 is further shown having an implant 1606. An insertion mandrel 1608 is depicted extending through a portion of the handle 1602, extending entirely through the shaft 1604, and fully extended into the implant 1606.

Turning now to the shaft 1604, the shaft 1604 is depicted having an inner diameter 1610, a distal end 1612 and a proximal end 1614. The insertion mandrel 1608 can be threaded through the inner diameter 1610 of the shaft 1604.

For the purposes of this description, the proximal end 1614 is an end of the shaft 1604 closest to an operator or a user of the fusion system 1600 during implantation while the distal end 1612 is an end of the shaft 1604 furthest from an operator or a user of the fusion system 1600 during implantation. As shown, the distal end 1612 is the end of the shaft 1604 near the implant 1606 and the proximal end 1614 is the end of the shaft 1604 near the handle 1602.

The implant 1606 can be attached to the shaft 1604 with a pivoting attachment joint 1616. The pivoting attachment joint 1616 can be a portion of the distal end 1612 of the shaft 1604. The pivoting attachment joint 1616 can affix or lock the implant 1606 to the shaft 1604 based on the insertion mandrel 1608 being extended through or into the pivoting attachment joint 1616 and deforming the pivoting attachment joint 1616 outward into the implant 1606.

The pivoting attachment joint 1616 of the shaft 1604 can release or detach the implant 1606 based on the insertion mandrel 1608 being retracted into the distal end 1612 of the shaft 1604 relieving stress from the pivoting attachment joint 1616 and allowing the pivoting attachment joint 1616 to return inward, away from the implant 1606, into a pre-deformed state. The shaft 1604 is further depicted including an indicator 1618.

The indicator 1618 can be directly coupled to the insertion mandrel 1608 within the shaft 1604 and extend from the insertion mandrel 1608 through a groove in the shaft 1604. The indicator 1618 can move along with the insertion mandrel 1608 and can indicate the current position of the insertion mandrel 1608 within the shaft 1604 and within the implant 1606.

The indicator 1618 can also be used to manually manipulate the insertion mandrel 1608 by moving it relative to the shaft 1604 during implantation by an operator or a user. Turning now to the handle 1602, the handle 1602 is depicted including an inner piece 1620 and an outer piece 1622.

The inner piece 1620 of the handle 1602 can be fitted within the outer piece 1622 of the handle 1602. The inner piece 1620 can extend out of the outer piece 1622 ensuring that the outer piece 1622 and the inner piece 1620 can be manipulated independently by an operator or a user.

It is contemplated that the inner piece 1620 can be pulled out from, and relative to, the outer piece 1622. It is further contemplated that the inner piece 1620 can be rotated within, and relative to, the outer piece 1622.

The inner piece 1620 and the outer piece 1622 can also be manipulated together meaning that the inner piece 1620 and the outer piece 1622 can be twisted or otherwise moved together as a single handle 1602. The outer piece 1622 of the handle 1602 can be in direct contact with and rigidly affixed to the proximal end 1614 of the shaft 1604.

The inner piece 1620 of the handle 1602 can be in direct moveable contact with the insertion mandrel 1608. The inner piece 1620 is further depicted including a cavity 1624.

Turning now to the insertion mandrel 1608, the insertion mandrel 1608 in depicted as a cannulated mandrel having a tube cavity extending entirely through the insertion mandrel 1608 and open at both ends. The insertion mandrel 1608 is further shown having a smooth section 1626 near the distal end 1612 of the shaft 1604.

The insertion mandrel 1608 further includes a helical screw 1628. The helical screw 1628 can extend from the smooth section 1626, through the shaft 1604, through the outer piece 1622 of the handle 1602 and through the inner piece 1620 of the handle 1602.

The helical screw 1628 of the insertion mandrel 1608 can be mated with the inner piece 1620 of the handle 1602. The insertion mandrel 1608 can be extended or retracted by rotating the inner piece 1620 of the handle 1602 relative to the outer piece 1622 of the handle 1602 and relative to the shaft 1604.

The insertion mandrel 1608 can move longitudinally within the shaft 1604 based on the inner piece 1620 of the handle 1602 being twisted or based on the inner piece 1620 of the handle 1602 being pulled out of or away from the outer piece 1622 of the handle 1602. The insertion mandrel 1608 can extend out of the pivoting attachment joint 1616 of the distal end 1612 of the shaft 1604.

The insertion mandrel 1608 can further be fully retracted into the distal end 1612 of the shaft 1604 and can be retracted into the cavity 1624 of the inner piece 1620 of the handle 1602. It has been discovered that the helical screw 1628 coupled to the inner piece 1620 of the handle 1602 enables the insertion mandrel 1608 to be controllably retracted from the implant 1606. The insertion mandrel 1608 can be retracted partially or fully into the distal end 1612 of the shaft 1604.

The insertion mandrel 1608 is further depicted having a piston 1630 formed on or affixed thereto. The piston 1630 can be seen to include a seal 1632 such as an O-ring between the inner surface of the cavity 1624 and the piston 1630. The piston 1630 can decrease the volume of the cavity 1624 based on the insertion mandrel 1608 being retracted into the cavity 1624 by rotating the inner piece 1620 of the handle 1602 relative to the outer piece 1622.

The insertion mandrel 1608 can further be utilized to inserting the expansion mandrel 704 of FIG. 7, for example, into the implant 1606. That is, the insertion mandrel 1608 could be threaded within the mandrel inner cavity 1504 of FIG. 15. The helical screw 1628 can further be used to transfer rotational input to linearly force the expansion mandrel 704 into the implant 1606.

Turning now to the implant 1606, the implant 1606 can consist of segments 1634 with an inner lumen 1636 extending through the segments 1634. It is contemplated that the segments 1634 can be coupled to one another with a flexible guide for forcing the segments 1634 into a curved configuration as the insertion mandrel 1608 is retracted from the segments 1634 into the distal end 1612 of the shaft 1604.

The insertion mandrel 1608 can be extended and retracted within the lumen 1636 of the segments 1634. When the insertion mandrel 1608 is extended through the lumen 1636 into the segments 1634, the insertion mandrel 1608 can force the segments 1634 into a straight configuration. When the insertion mandrel 1608 is retracted from any one of the segments 1634, the segment 1634 without the insertion mandrel 1608 therein can assume, or be forced, into a curved configuration with the flexible guide.

The implant 1606 can further be pivotable based on the insertion mandrel 1608 being retracted into the last of the segments 1634 while maintaining the deformation of the pivoting attachment joint 1616. That is, the implant 1606 can pivot on the pivoting attachment joint 1616 when the insertion mandrel 1608 is retracted to a point where the insertion mandrel 1608 no longer impinges on the segments 1634 of the implant 1606 and still deforms the pivoting attachment joint 1616.

Figure 17:
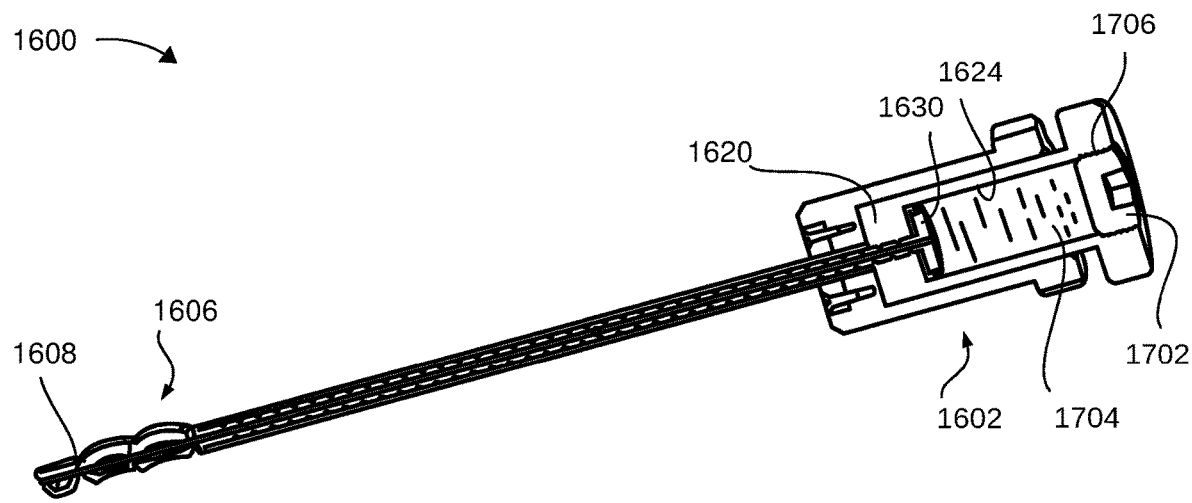

Referring now to FIG. 17, therein is shown a cross-sectional isometric view of the fusion system 1600 of FIG. 16 in a filled state. The fusion system 1600 can be seen to further include a cap 1702 and a biologic, such as bone graft material 1704, within the cavity 1624 of the handle 1602.

For ease of description, the disclosure relies on the term "bone graft material 1704"; however, it is contemplated that the bone graft material 1704 can be materials such as autograft, allograft, other osteoconductive material, or other bone growth material.

As will be appreciated, the cap 1702 can be remove ably affixed to the inner piece 1620 of the handle 1602 with a threaded connection 1706. The threaded connection between the cap 1702 and the inner piece 1620 of the handle 1602 should contain the bone graft material 1704 under pressure within the cavity 1624 without leaking.

The bone graft material 1704 can fill the cavity 1624 between the piston 1630 and the cap 1702. The bone graft material 1704 can be introduced through the tube cavity of the insertion mandrel 1608 because the tube cavity extends through the piston 1630 and through the insertion mandrel 1608 providing an open path for the bone graft material 1704 to flow from the cavity 1624 out of the insertion mandrel 1608 near the implant 1606.

Figure 18:
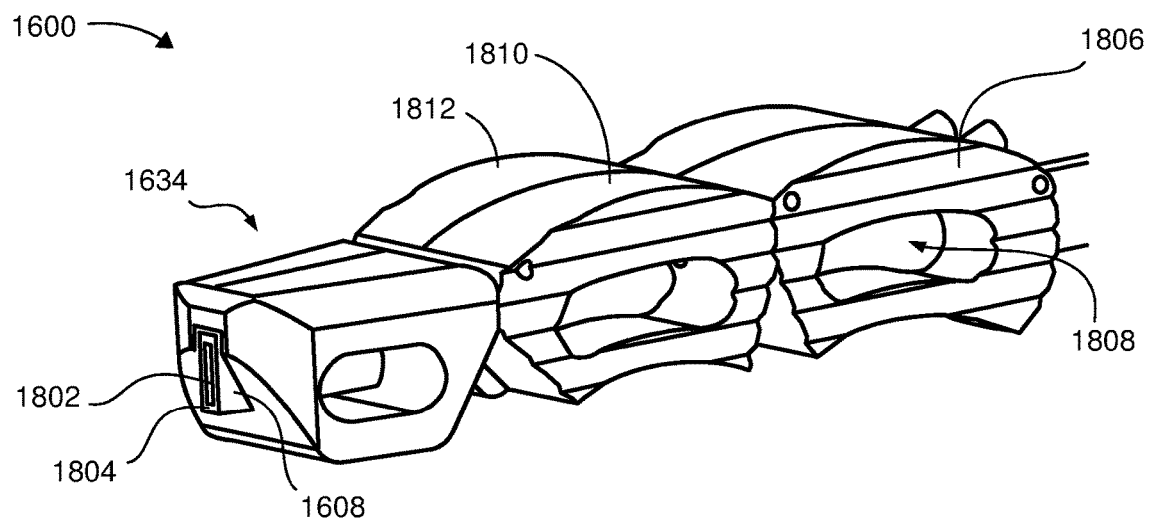

Referring now to FIG. 18, therein is shown an isometric view of Section C of FIG. 16. Section C depicts a portion of the fusion system 1600 wherein the insertion mandrel 1608 is extended through the distal end 1612 of FIG. 16 of the shaft 1604 of FIG. 16 and into the segments 1634, is non-circular. Importantly it has been discovered that the non-circular shape of the insertion mandrel 1608 is effective at transferring torque from the insertion mandrel 1608 to the implant 1606 of FIG. 16.

Specifically, the operator or user can twist the shaft 1604 or the handle 1602 of FIG. 16 transferring torque to the non-circular insertion mandrel 1608, the non-circular insertion mandrel 1608 would then transfer this torque to the implant 1606.

The insertion mandrel 1608 is shown partially extended out from the distal segment. The insertion mandrel 1608 can include a tube cavity 1802, which is shown as non-circular however it is contemplated that the tube cavity 1802 can be a circular shape.

The insertion mandrel 1608 is further shown having a flat end surface 1804 and the flat end surface 1804 can be flush with a portion of the segments 1634 and extended out from another portion of the segments 1634.

The segments 1634 are shown having ridges 1806 and holes 1808. The ridges 1806 can stabilize the implant 1606 during implantation and can help guide the implant 1606 into a proper position. The holes 1808 can be used to provide bone graft material or bone growth material.

Each of the segments 1634 can include a segment upper 1810 and a segment lower 1812. The flexible guide 120 of FIG. 1, for example, can extend continuously through the segment upper 1810 and the segment lower 1812 of each of the segments 1634.

The implant 1606 can be expanded by moving the segment upper 1810 and the segment lower 1812 away from each other. When this expansion is performed during implantation of the fusion system 1600, the segment upper 1810 and the segment lower 1812 will expand in the spine's longitudinal direction.

Figure 19:
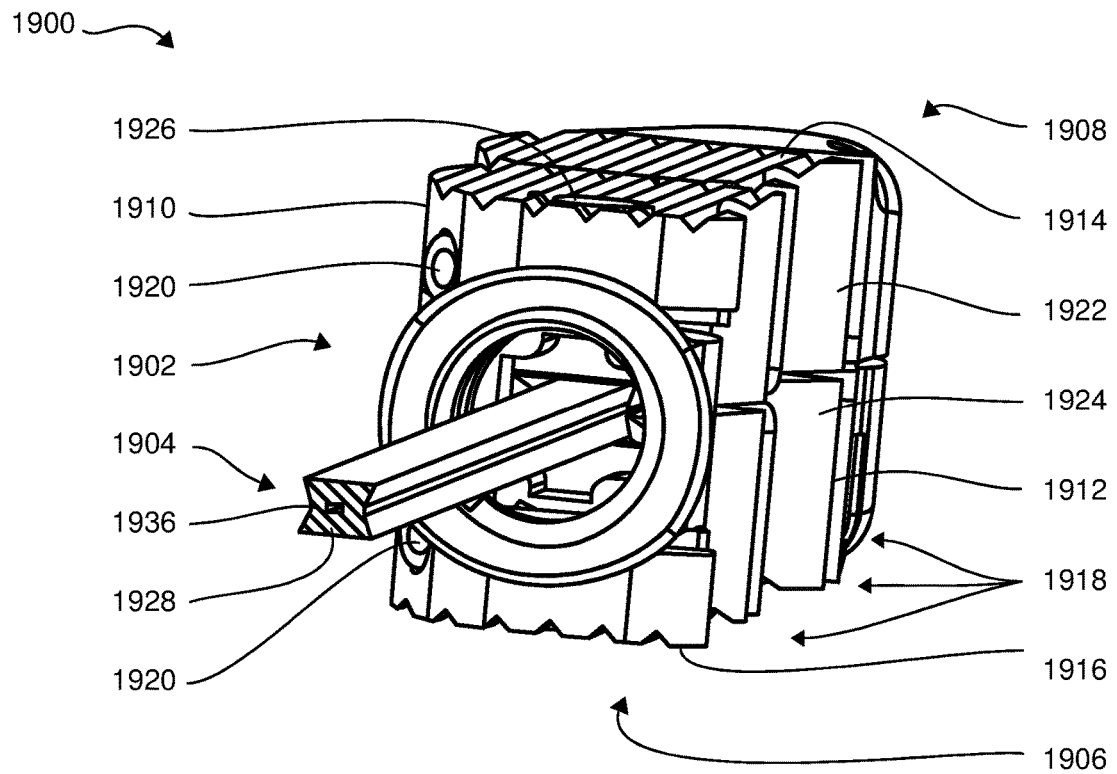
FIG. 19 is an isometric view of the fusion system in a third embodiment and in a straight configuration.

Referring now to FIG. 19, therein is shown an isometric view of the fusion system 1900 in a third embodiment and in a straight configuration. The fusion system 1900 is depicted having an implant 1902 mechanically coupled to a delivery tool 1904.

The implant 1902 is contemplated to be an expandable multi-segment interbody fusion implant for insertion into vertebral disk space. The implant 1902 can pivot at the interface between the delivery tool 1904 and the implant 1902.

For the purposes of this disclosure, the implant 1902 will be described with regard to a proximal end 1906, a distal end 1908, an outer curved surface 1910, an inner curved surface 1912, a top surface 1914, and a bottom surface 1916.

The proximal end 1906 is the end of the implant 1902 closest to and coupled with the delivery tool 1904. The proximal end 1906 will also be closer to an operator or user during implantation of the implant 1902.

The distal end 1908 is the end of the implant 1902 opposite from the proximal end 1906 when the implant 1902 is in the straight configuration. The outer curved surface 1910 and the inner curved surface 1912 can each extend between the top surface 1914 and the bottom surface 1916 of the implant 1902.

The outer curved surface 1910 can provide a larger area, when the implant 1902 is in the curved configuration, than the inner curved surface 1912. The implant 1902 is shown having three segments 1918. The segments 1918 can be made of a bio-compatible material.

For ease of description, the segments 1918 can be referred to as the proximal segment, the distal segment, and the middle segment. However, it is to be understood that the disclosure is not limited to a specific number of segments unless otherwise claimed.

The segments 1918 can be coupled together with a flexible guide 1920. The flexible guide 1920 can extend through the segments 1918 and can have a pre-defined curved shape.

The flexible guide 1920 can be a flexible wire, ribbon, or cable. It is contemplated that the flexible guide 1920 may be made from a shape memory or super elastic material. These can include both shape memory alloys, such as nitinol, and shape memory polymers. The shape memory alloys and polymers should be understood to have the ability to return from a deformed state to an original and permanent shape induced by an external stimulus, such as a temperature or pressure change.

The flexible guide 1920 can be made from a bio-compatible material such as stainless steel. Further, the flexible guide 1920 can have a pre-defined curved shape, as shown in FIG. 5, above.

Each of the segments 1918 can include a segment upper 1922 and a segment lower 1924. The flexible guide 1920 can extend continuously through the segment upper 1922 and the segment lower 1924 of each of the segments 1918 and can wrap around the distal end 1908.

The implant 1902 can be expanded by moving the segment upper 1922 and the segment lower 1924 away from each other. When this expansion is performed during implantation of the fusion system 1900, the segment upper 1922 and the segment lower 1924 will expand in the spine's longitudinal direction.

As depicted in FIG. 19, the implant 1902 is in a non-expanded configuration with the segment upper 1922 and the segment lower 1924 in direct contact with one another. The segment upper 1922 and the segment lower 1924 can be expanded with an expansion mandrel and held to one another with flexible connectors, which are depicted, for example, in the expanded configuration of FIG. 7.

The proximal segment is shown having a pivoting attachment joint 1926. The attachment joint 1926 is pivotally coupled to the delivery tool 1904 containing an insertion mandrel 1928. The insertion mandrel 1928 can have a non-circular cross-section in order to transmit torque between the implant 1902 and the delivery tool 1904.

As depicted, the insertion mandrel 1928 is depicted having lines representing cut surfaces. The insertion mandrel 1928 can have a cross-sectional shape of a double dovetail. The double dovetail can prevent the implant 1902 from prematurely entering the expanded configuration during insertion.

The insertion mandrel 1928 can extend through the segments 1918 of the implant 1902 to impart the straight configuration to the segments 1918 by temporarily deforming the flexible guide 1920. As the insertion mandrel 1928 is removed from the segments 1918, the flexible guide 1920 will return to the pre-defined curved shape and the segments 1918 will enter the curved configuration of FIG. 4, for example.

The insertion mandrel 1928 is further shown having a tube cavity 1936, which is shown as non-circular however it is contemplated that the tube cavity 1936 can be a circular shape. The tube cavity 1936 can be used to inject biologics into the implant 1902.

Figure 20:
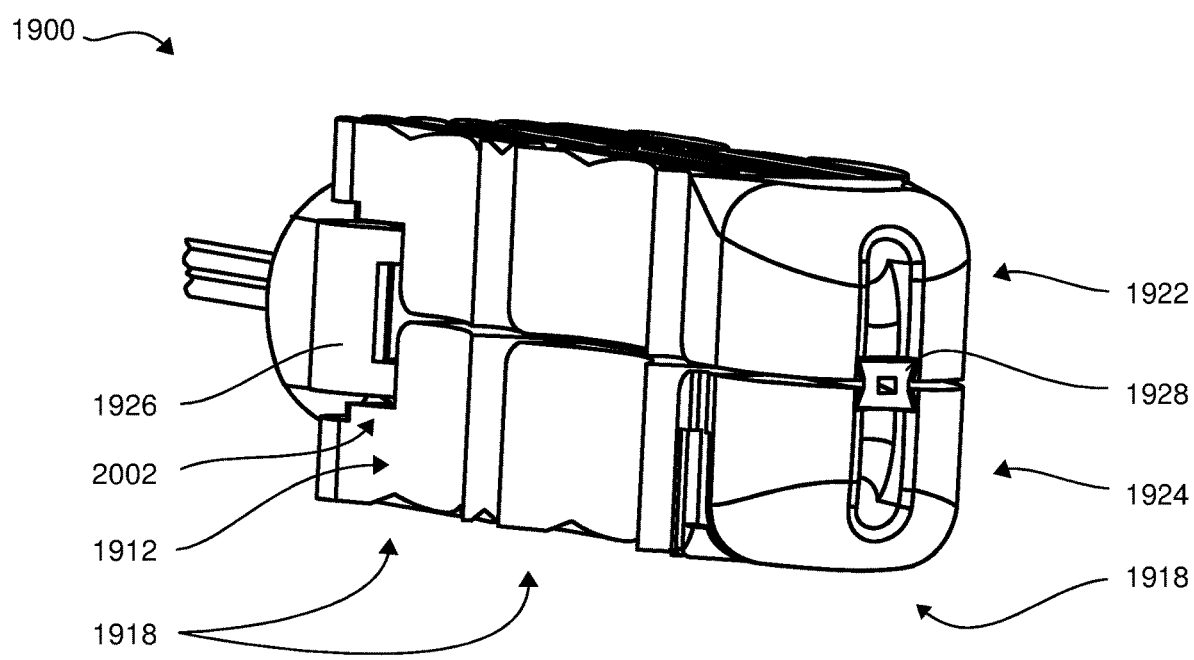
FIG. 20 is an isometric view of the fusion system of FIG. 19.

Referring now to FIG. 20, therein is shown an isometric view of the fusion system 1900 of FIG. 19. The fusion system 1900 is shown having the insertion mandrel 1928 with a double dovetail cross-section.

The double dovetail cross-section can keep the segment upper 1922 and the segment lower 1924 from separating from each other while the insertion mandrel 1928 remains extended therethrough. Once the insertion mandrel 1928 is removed from each of the segments 1918, the segment upper 1922 and the segment lower 1924 are no longer restricted by the shape of the insertion mandrel 1928 and can be moved apart, for example by the expansion mandrel 704 of FIG. 7.

The delivery tool 1904 can pivot about the attachment joint 1926 and can pivot towards the inner curved surface 1912 of the segments 1918 by pivoting through a pivot recess 2002. The pivot recess 2002 can provide space for the delivery tool 1904 to move between the segment upper 1922 and the segment lower 1924 near the attachment joint 1926 of the proximal segment.

Figure 21:
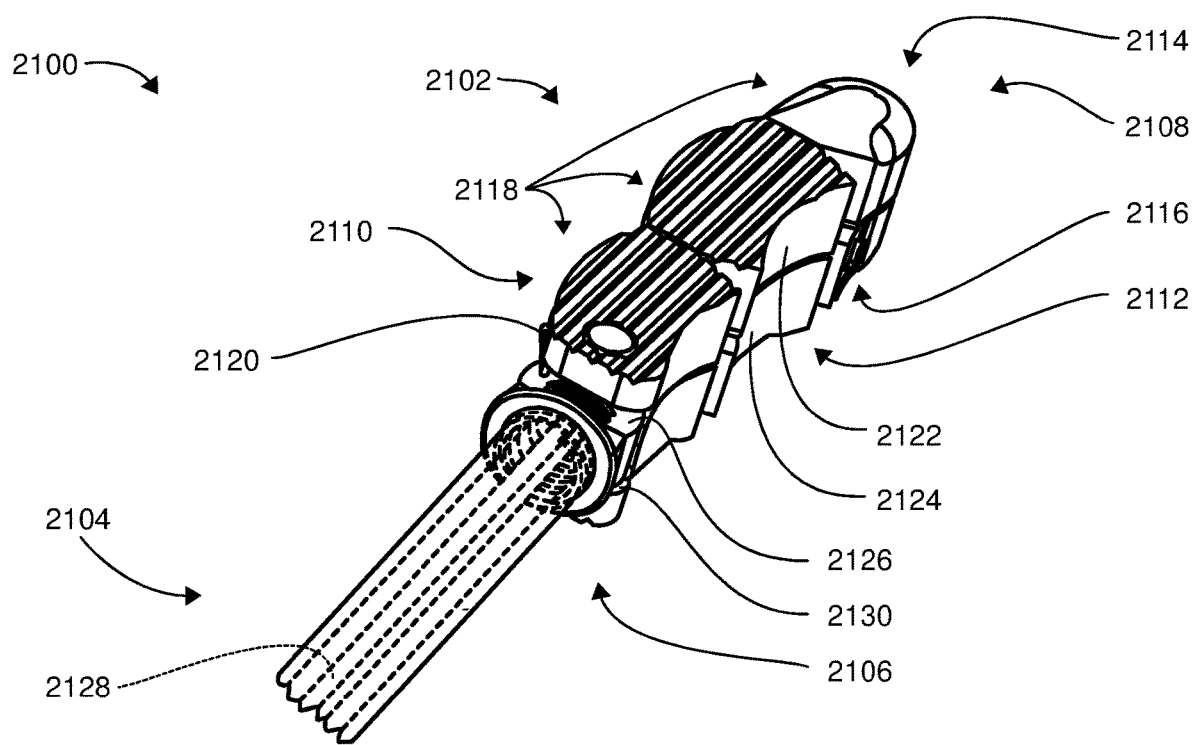
FIG. 21 is an isometric view of the fusion system in a fourth embodiment and in a straight configuration.

Referring now to FIG. 21, therein is shown an isometric view of the fusion system 2100 in a fourth embodiment and in a straight configuration. The fusion system 2100 is depicted having an implant 2102 mechanically coupled to a delivery tool 2104.

The implant 2102 is contemplated to be an expandable multi-segment interbody fusion implant for insertion into vertebral disk space. The implant 2102 can pivot at the interface between the delivery tool 2104 and the implant 2102.

For the purposes of this disclosure, the implant 2102 will be described with regard to a proximal end 2106, a distal end 2108, an outer curved surface 2110, an inner curved surface 2112, a top surface 2114, and a bottom surface 2116.

The proximal end 2106 is the end of the implant 2102 closest to and coupled with the delivery tool 2104. The proximal end 2106 will also be closer to an operator or user during implantation of the implant 2102.

The distal end 2108 is the end of the implant 2102 opposite from the proximal end 2106 when the implant 2102 is in the straight configuration. The outer curved surface 2110 and the inner curved surface 2112 can each extend between the top surface 2114 and the bottom surface 2116 of the implant 2102.

The outer curved surface 2110 can provide a larger area, when the implant 2102 is in the curved configuration, than the inner curved surface 2112. The implant 2102 is shown having three segments 2118. The segments 2118 can be made of a bio-compatible material.

For ease of description, the segments 2118 can be referred to as the proximal segment, the distal segment, and the middle segment. However, it is to be understood that the disclosure is not limited to a specific number of segments unless otherwise claimed.

The segments 2118 can be coupled together with a flexible guide 2120. The flexible guide 2120 can extend through the segments 2118 and can have a pre-defined curved shape.

The flexible guide 2120 can be a flexible wire, ribbon, or cable. It is contemplated that the flexible guide 2120 may be made from a shape memory or super elastic material. These can include both shape memory alloys, such as nitinol, and shape memory polymers. The shape memory alloys and polymers should be understood to have the ability to return from a deformed state to an original and permanent shape induced by an external stimulus, such as a temperature or pressure change.

The flexible guide 2120 can be made from a bio-compatible material such as stainless steel. Further, the flexible guide 2120 can have a pre-defined curved shape, as shown in FIG. 5, above.

Each of the segments 2118 can include a segment upper 2122 and a segment lower 2124. The flexible guide 2120 can extend continuously through the segment upper 2122 and the segment lower 2124 of each of the segments 2118 and can wrap around the distal end 2108.

The implant 2102 can be expanded by moving the segment upper 2122 and the segment lower 2124 away from each other. When this expansion is performed during implantation of the fusion system 2100, the segment upper 2122 and the segment lower 2124 will expand in the spine's longitudinal direction.

As depicted in FIG. 21, the implant 2102 is in a non-expanded configuration with the segment upper 2122 and the segment lower 2124 in direct contact with one another. The segment upper 2122 and the segment lower 2124 can be expanded with the expansion mandrel 2402 of FIG. 24 and held to one another with flexible connectors, which are depicted, for example, in the expanded configuration of FIG. 7.

The proximal segment is shown having a pivoting attachment joint 2126. The attachment joint 2126 is pivotally coupled to the delivery tool 2104 containing an insertion mandrel 2128. The insertion mandrel 2128 can have a non-circular cross-section in order to transmit torque between the implant 2102 and the delivery tool 2104.

The insertion mandrel 2128 can extend through the segments 2118 of the implant 2102 to impart the straight configuration to the segments 2118 by temporarily deforming the flexible guide 2120. As the insertion mandrel 2128 is removed from the segments 2118, the flexible guide 2120 will return to the pre-defined curved shape and the segments 2118 will enter the curved configuration of FIG. 4, for example.

The delivery tool 2104 can pivot about the attachment joint 2126 and can pivot towards the inner curved surface 2112 of the segments 2118 by pivoting through a pivot recess 2130. The pivot recess 2130 can provide space for the delivery tool 2104 to move between the segment upper 2122 and the segment lower 2124 near the attachment joint 2126 of the proximal segment.

Figure 22:
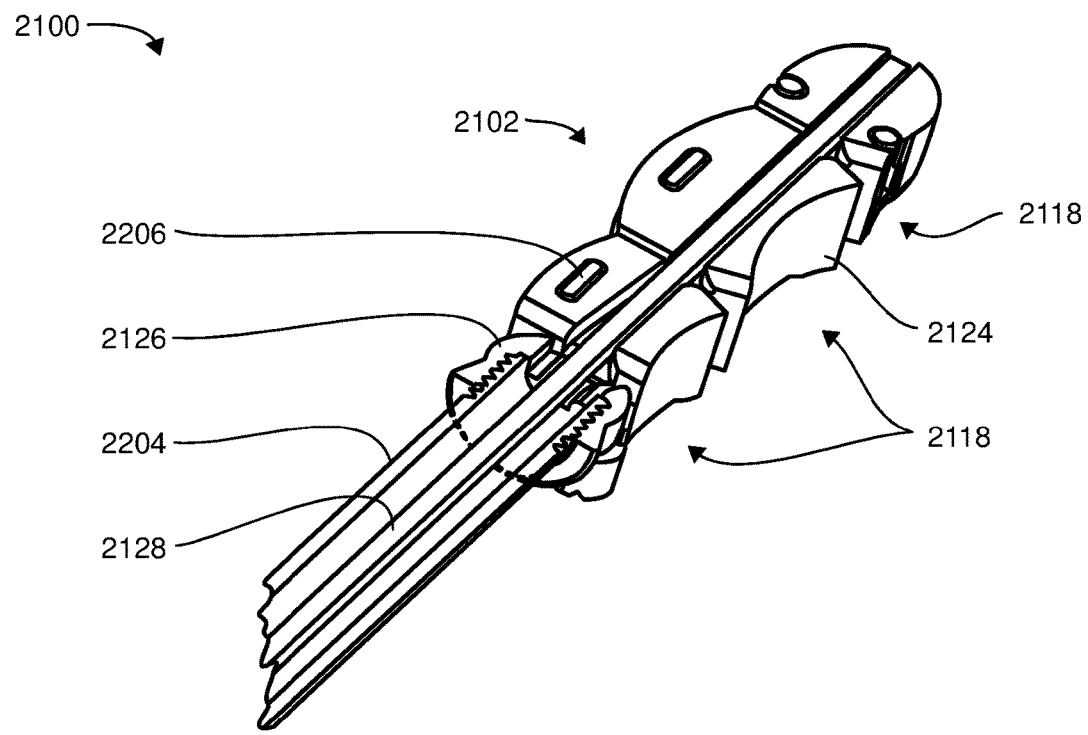
FIG. 22 is a cross-sectional isometric view of the fusion system of FIG. 21.

Referring now to FIG. 22, therein is shown a cross-sectional isometric view of the fusion system 2100 of FIG. 21. The insertion mandrel 2128 is shown extended through the segments 2118 imparting the straight configuration to the implant 2102.

The insertion mandrel 2128 can be directed and supported by a shaft 2204. The shaft 2204 can be screwed into the attachment joint 2126 of the implant 2102. When the insertion mandrel 2128 is removed from the shaft 2204, the expansion mandrel 2402 of FIG. 24, for example, can be inserted into the segments 2118 through the shaft 2204 in order to expand the segments 2118.

The segment uppers 2122 of FIG. 21 and the segment lowers 2124 are coupled to one another with expansion limiters 2206. The expansion limiters 2206 can be formed integrally with the segments 2118 or can be coupled to the segments 2118 during manufacture. The expansion limiters 2206 can prevent the segment upper 2122 from expanding away from the segment lower 2124, more than a limit imposed by the physical structure of the extension limiters 2206 and can prevent separation of the segments 2118.

Figure 23:
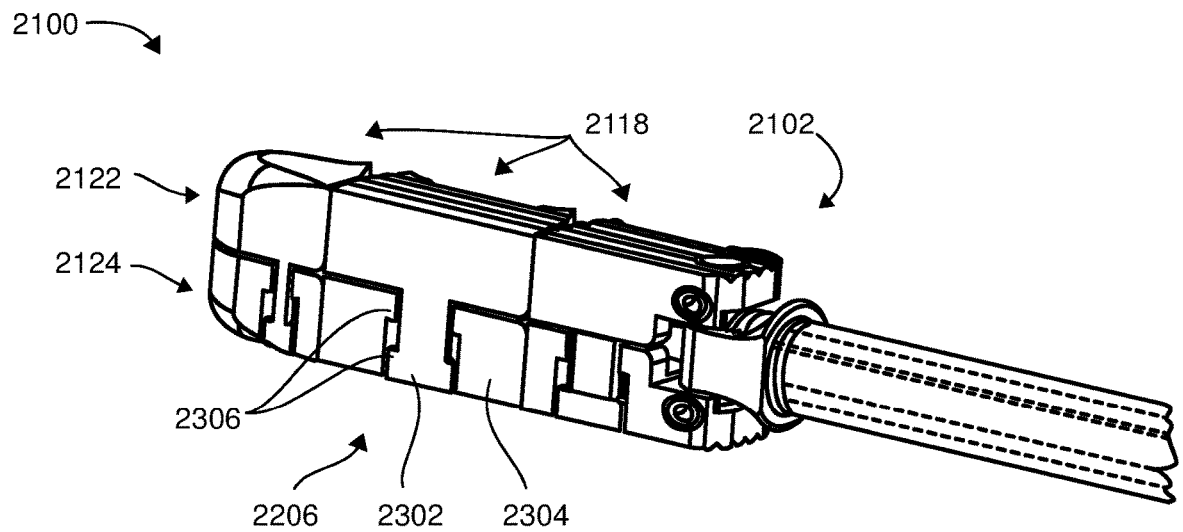
FIG. 23 is a cross-sectional isometric view of the fusion system of FIG. 21.

Referring now to FIG. 23, therein is shown a cross-sectional isometric view of the fusion system 2100 of FIG. 21. The outer curved surface 2110 of FIG. 21 has been removed from the segments 2118 exposing the expansion limiters 2206.

The expansion limiters 2206 are shown with a male limiter 2302 extending down into a female limiter 2304. The male limiter 2302 is prevented from moving out of the female limiter 2304 due to overhangs 2306 on both the male limiter 2302 and the female limiter 2304.

The segment upper 2122 and the segment lower 2124 can expand away from each other by the amount of distance between the overhangs 2306 of the male limiter 2302 and the female limiter 2304 when the implant 2102 is in an unexpanded configuration. It is contemplated that the expansion limiters 2206 can be used in combination with the flexible connection 702 of FIG. 7 to provide smooth operation between expanded and unexpanded configurations.

Figure 24:
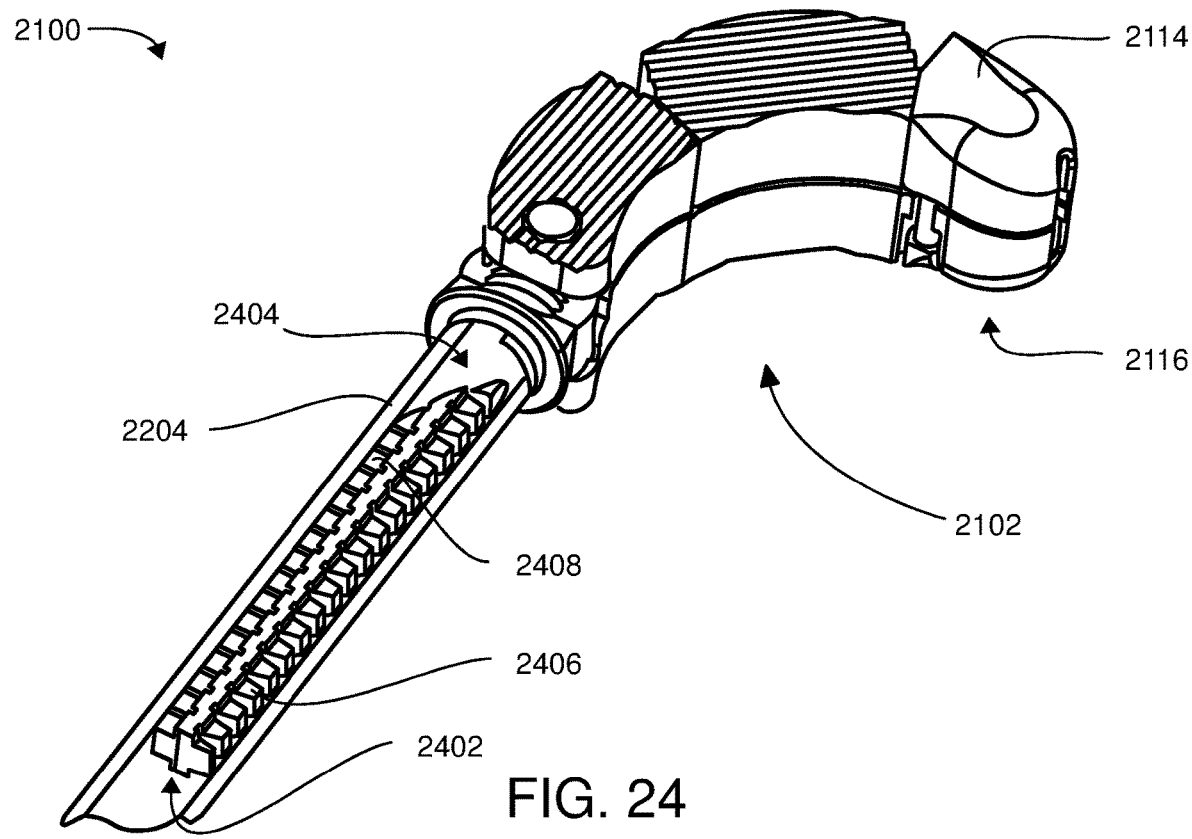
FIG. 24 is an isometric view of the fusion system of FIG. 21 in a curved configuration.

Referring now to FIG. 24, therein is shown an isometric view of the fusion system 2100 of FIG. 21 in a curved configuration. The insertion mandrel 2128 of FIG. 21 has been withdrawn from the shaft 2204 and has been replaced with an expansion mandrel 2402.

The expansion mandrel 2402 is shown having a sloped front side 2404, wedges 2406, and blocks 2408. The expansion mandrel 2402 can be formed with the wedges 2406 and the blocks 2408 offset so that the edges of the wedges 2406 aligns with the middle of the blocks 2408 and the edges of the blocks 2408 align with the middle of the wedges 2406.

This staggered structure of the wedges 2406 and the blocks 2408 enables the expansion mandrel 2402 to flex readily within the implant 2102 while maintaining expansion force out toward the top surface 2114 and the bottom surface 2116 as the expansion mandrel 2402 is forced into the implant 2102. The sloped front side 2404 has been discovered to enable the expansion mandrel 2402 to be inserted into the implant 2102 with greater ease as the need for precise alignment is decreased.

Figure 25:
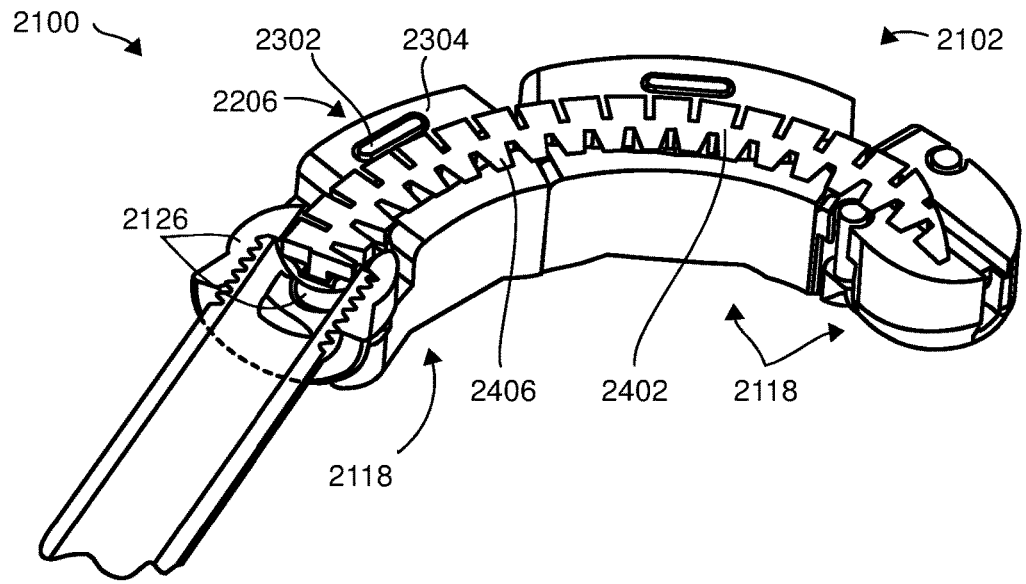
FIG. 25 is a cross-section isometric view of the fusion system of FIG. 24.

Referring now to FIG. 25, therein is shown a cross-section isometric view of the fusion system 2100 of FIG. 21 in an expanded configuration. The implant 2102 is shown having the expansion mandrel 2402 fully inserted within the segments 2118. The attachment joint 2126 can be seen pivotally coupled to the implant 2102.

The expansion limiters 2206 will be fully expanded with the overhangs 2306 of FIG. 23 of the male limiter 2302 and the female limiter 2304 in direct contact while the implant 2102 is in the expanded configuration. The wedges 2406 of the expansion mandrel 2402 are shown closer together but not contacting as in other embodiments of this disclosure.

Figure 26:
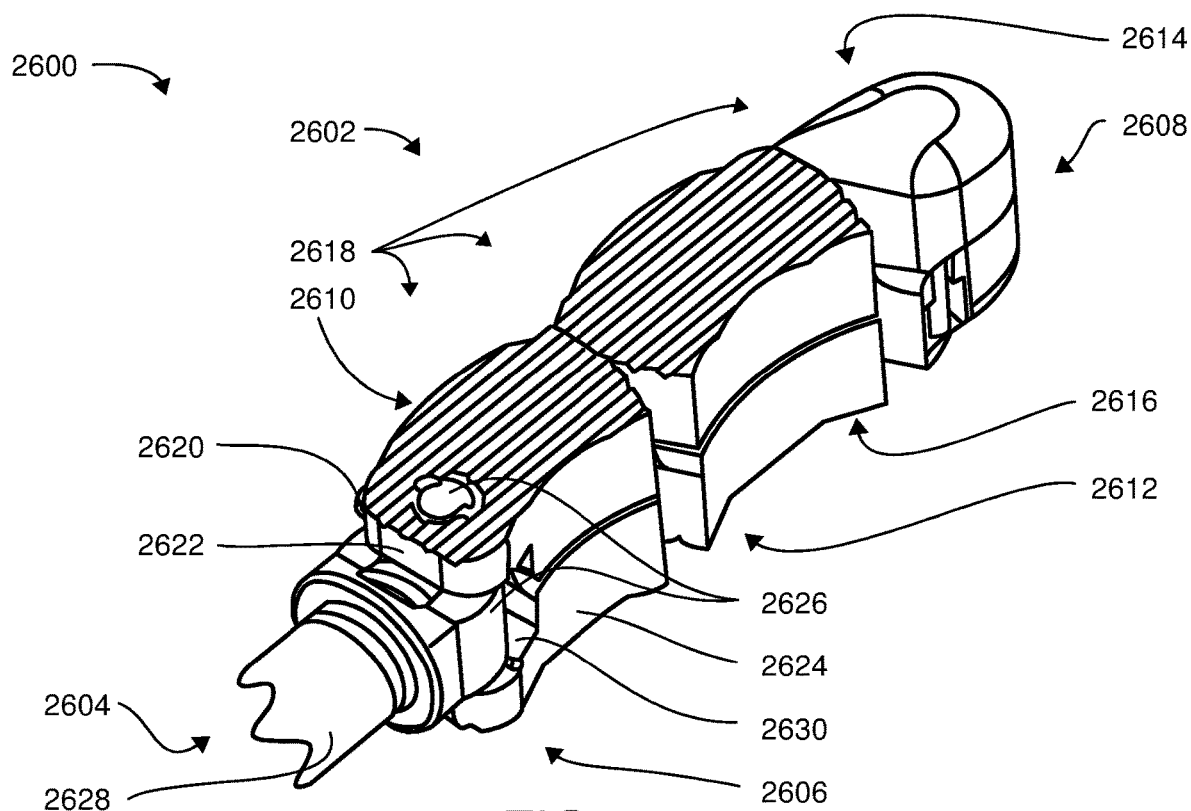
FIG. 26 is an isometric view of the fusion system in a fifth embodiment and in a straight configuration.

Referring now to FIG. 26, therein is shown an isometric view of the fusion system 2600 in a fifth embodiment and in a straight configuration. The fusion system 2600 is depicted having an implant 2602 mechanically coupled to a delivery tool 2604.

The implant 2602 is contemplated to be an expandable multi-segment interbody fusion implant for insertion into vertebral disk space. The implant 2602 can pivot at the interface between the delivery tool 2604 and the implant 2602.

For the purposes of this disclosure, the implant 2602 will be described with regard to a proximal end 2606, a distal end 2608, an outer curved surface 2610, an inner curved surface 2612, a top surface 2614, and a bottom surface 2616.

The proximal end 2606 is the end of the implant 2602 closest to and coupled with the delivery tool 2604. The proximal end 2606 will also be closer to an operator or user during implantation of the implant 2602.

The distal end 2608 is the end of the implant 2602 opposite from the proximal end 2606 when the implant 2602 is in the straight configuration. The outer curved surface 2610 and the inner curved surface 2612 can each extend between the top surface 2614 and the bottom surface 2616 of the implant 2602.

The outer curved surface 2610 can provide a larger area, when the implant 2602 is in the curved configuration, than the inner curved surface 2612. The implant 2602 is shown having three segments 2618. The segments 2618 can be made of a bio-compatible material.

For ease of description, the segments 2618 can be referred to as the proximal segment, the distal segment, and the middle segment. However, it is to be understood that the disclosure is not limited to a specific number of segments unless otherwise claimed.

The segments 2618 can be coupled together with a flexible guide 2620. The flexible guide 2620 can extend through the segments 2618 and can have a pre-defined curved shape.

The flexible guide 2620 can be a flexible wire, ribbon, or cable. It is contemplated that the flexible guide 2620 may be made from a shape memory or super elastic material. These can include both shape memory alloys, such as nitinol, and shape memory polymers. The shape memory alloys and polymers should be understood to have the ability to return from a deformed state to an original and permanent shape induced by an external stimulus, such as a temperature or pressure change.

The flexible guide 2620 can be made from a bio-compatible material such as stainless steel. Further, the flexible guide 2620 can have a pre-defined curved shape, as shown in FIG. 5, above.

Each of the segments 2618 can include a segment upper 2622 and a segment lower 2624. The flexible guide 2620 can extend continuously through the segment upper 2622 and the segment lower 2624 of each of the segments 2618 and can wrap around the distal end 2608.

The implant 2602 can be expanded by moving the segment upper 2622 and the segment lower 2624 away from each other. When this expansion is performed during implantation of the fusion system 2600, the segment upper 2622 and the segment lower 2624 will expand in the spine's longitudinal direction.

As depicted in FIG. 26, the implant 2602 is in a non-expanded configuration with the segment upper 2622 and the segment lower 2624 in direct contact with one another. The segment upper 2622 and the segment lower 2624 can be expanded with an expansion mandrel and held to one another with flexible connectors, which are depicted, for example, in the expanded configuration of FIGS. 30 and 31.

The delivery tool 2604 can pivot about the attachment joint 2626 and can pivot towards the inner curved surface 2612 of the segments 2618 by pivoting through a pivot recess 2630. The pivot recess 2630 can provide space for the delivery tool 2604 to move between the segment upper 2622 and the segment lower 2624 near the attachment joint 2626 of the proximal segment.

The shaft 2628 can be detached from the attachment joint 2626 with a threaded interconnection. The attachment joint 2626 can also be detached from the proximal segment once the implant 2602 is implanted.

Figure 27:
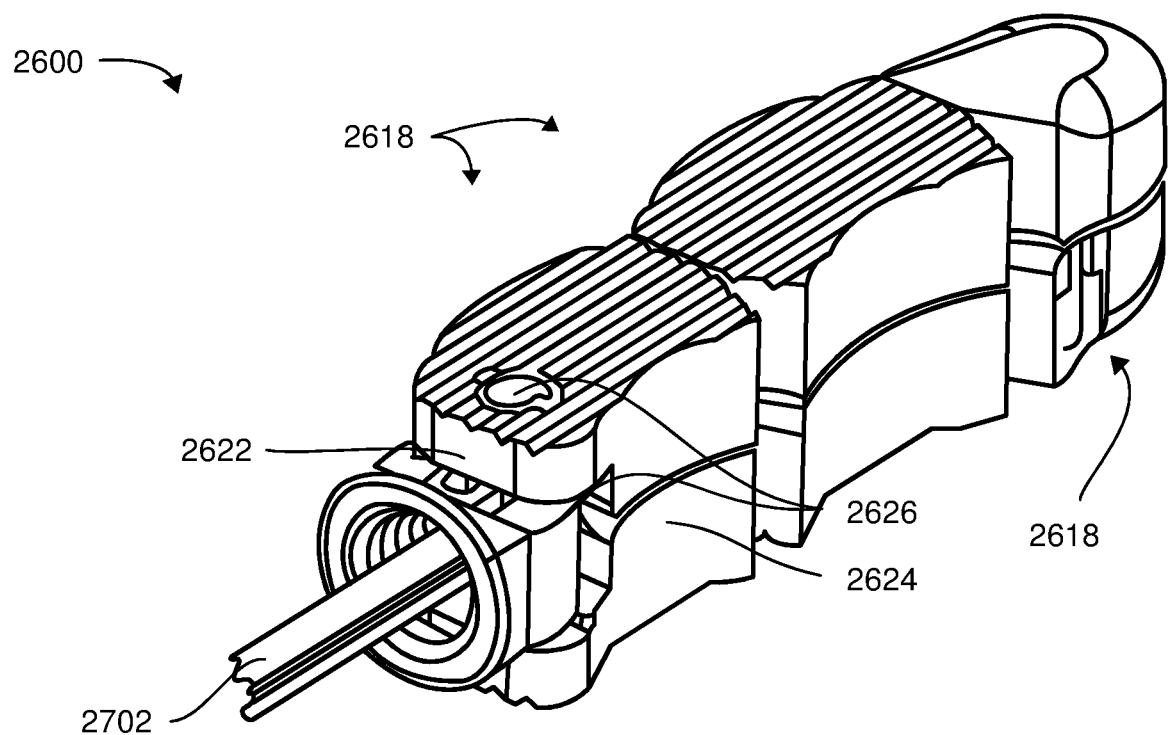
FIG. 27 is an isometric view of the fusion system of FIG. 26 with the shaft removed.

Referring now to FIG. 27, therein is shown an isometric view of the fusion system 2600 of FIG. 26 with the shaft 2628 of FIG. 26 removed. The shaft 2628 can be unthreaded from the attachment joint 2626.

The attachment joint 2626 is shown attached to the proximal segment with an insertion mandrel 2702 extended therethrough. The insertion mandrel 2702 is shown fully extended through the segments 2618.

Extending the insertion mandrel 2702 fully through the segments 2618 can ensure the segments 2618 are in the straight configuration by temporarily deforming the flexible guide 2620 of FIG. 26. As the insertion mandrel 2702 is removed from the segments 2618, the flexible guide 2620 will return to the pre-defined curved shape and the segments 2618 will enter the curved configuration of FIG. 28, for example.

Figure 29:
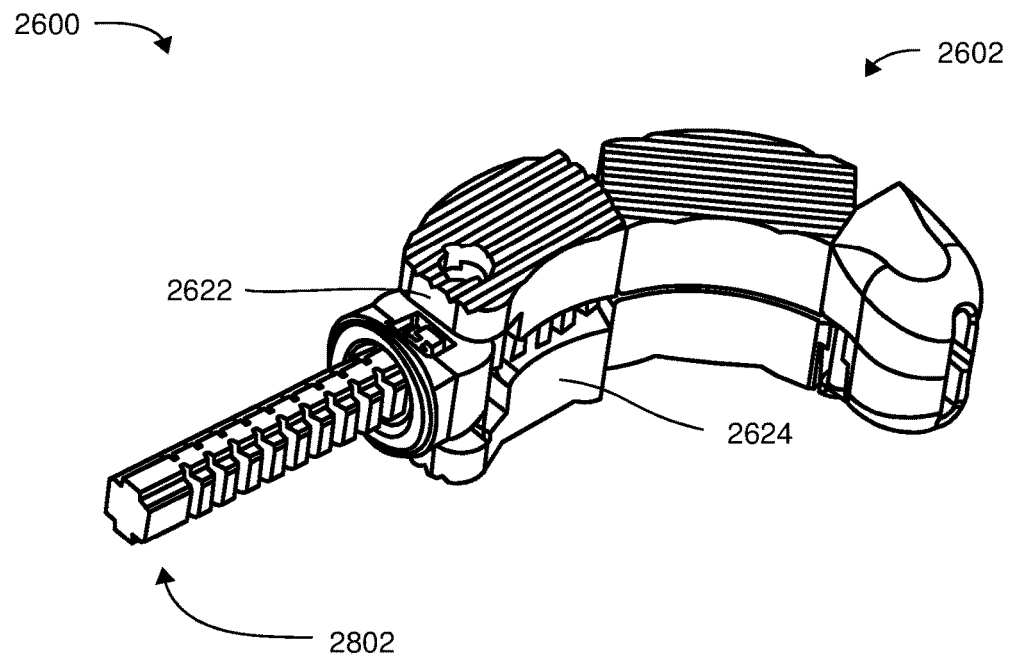
FIG. 29 is an isometric view of the fusion system of FIG. 28 in a partially expanded configuration.

The insertion mandrel 2702 is further shown with a double dovetail cross-section, as is shown, for example, in FIG. 29. The double dovetail can prevent the implant 2602 of FIG. 26 from prematurely entering the expanded configuration during insertion as both the segment upper 2622 and the segment lower 2624 can incorporate a female dovetail for mating with the insertion mandrel 2702. The double dovetail cross-section of the insertion mandrel 2702 can further transmit torque between the implant 2602 and the delivery tool 2604 of FIG. 26.

Figure 28:
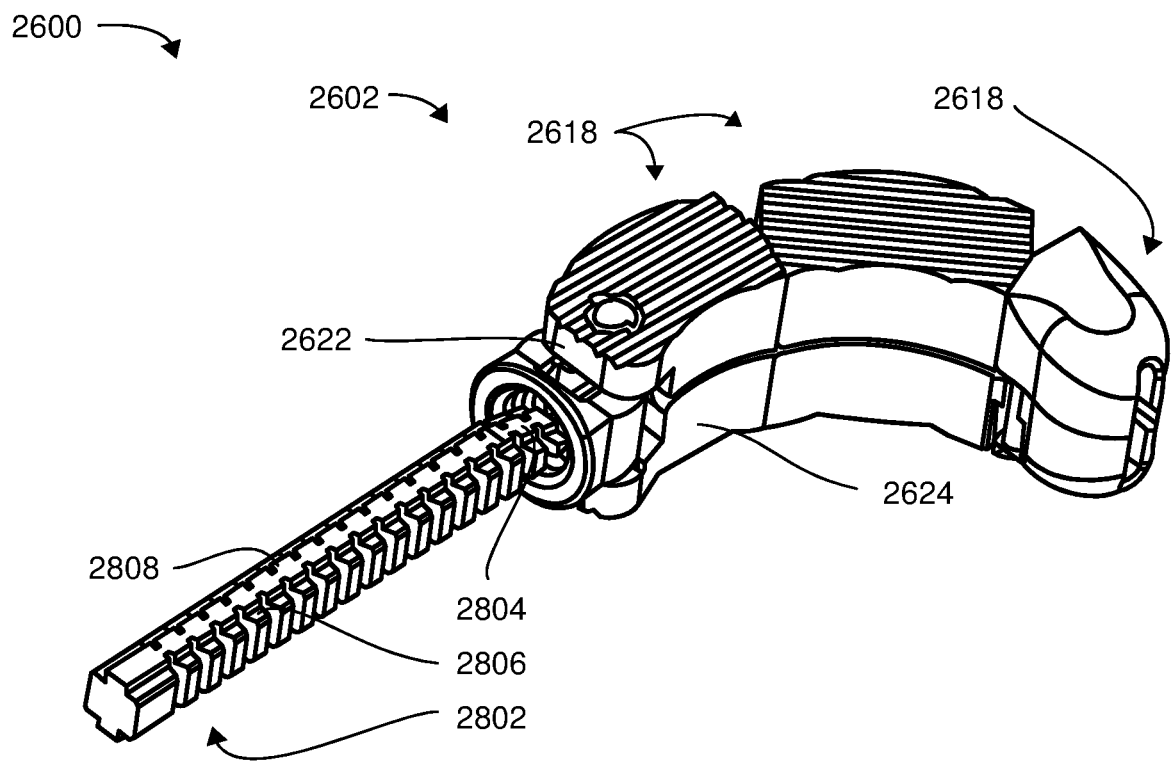
FIG. 28 is an isometric view of the fusion system in a curved configuration.

Referring now to FIG. 28, therein is shown an isometric view of the fusion system 2600 in a curved configuration. The insertion mandrel 2702 of FIG. 27 has been withdrawn from the implant 2602 and in its place, an expansion mandrel 2802 is shown as staged, ready for insertion into the implant 2602.

The expansion mandrel 2802 is shown having a sloped front side 2804, wedges 2806, and blocks 2808. The expansion mandrel 2802 can be formed with the wedges 2806 and the blocks 2808 aligned so that the edges of the wedges 2806 aligns with the edges of the blocks 2808 and the edges of the blocks 2808 align with the edges of the wedges 2806.

The sloped front side 2804 can slope down to the distal end of the expansion mandrel 2802. The sloped front side 2804 can slope down in a vertical direction, ninety degrees rotation from the plane through which the expansion mandrel 2802 and the segments 2618 curve in the curved configuration. The sloped front side 2804 can therefore force the segment upper 2622 up, away from the segment lower 2624, forcing the implant 2602 into the expanded configuration as the expansion mandrel 2802 is inserted into the implant 2602. The sloped front side 2804 has been discovered to enable the expansion mandrel 2802 to be inserted into the implant 2602 with greater ease as the need for precise alignment is decreased.

Referring now to FIG. 29, therein is shown an isometric view of the fusion system 2600 of FIG. 28 in a partially expanded configuration. The expansion mandrel 2802 is shown inserted into the proximal segment of the implant 2602.

The proximal segment is shown with the expansion mandrel 2802 between the segment upper 2622 and the segment lower 2624 forcing the segment upper 2622 away from the segment lower 2624 and placing the proximal segment in the expanded configuration. As the expansion mandrel 2802 is inserted between the middle and distal segments, the middle and distal segments will be placed into the expanded configuration.

Figure 30:
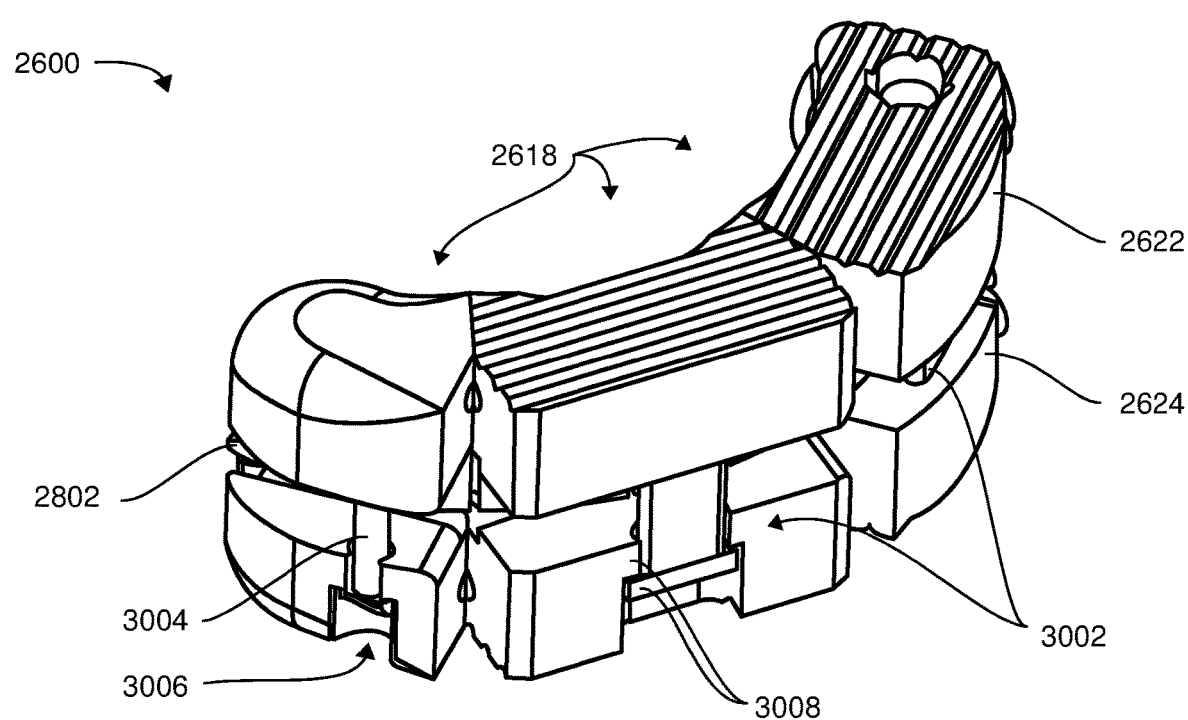
FIG. 30 is an outer cross-sectional isometric view of the fusion system of FIG. 26 in an expanded configuration.

Referring now to FIG. 30, therein is shown an outer cross-sectional isometric view of the fusion system 2600 of FIG. 26 in an expanded configuration. The outer curved surface 2610 of FIG. 26 has been removed from the segments 2618 exposing expansion limiters 3002 within the middle and distal segments. The proximal segment is further shown and contemplated to incorporate one of the expansion limiters 3002.

The segment upper 2622 and the segment lower 2624 for each segment 2618 have been moved apart by the expansion mandrel 2802 which has been inserted therebetween. The expansion limiters 3002 are shown with a male limiter 3004 extending down into a female limiter 3006. The male limiter 3004 is prevented from moving out of the female limiter 3006 due to overhangs 3008 on both the male limiter 3004 and the female limiter 3006.

The segment upper 2622 and the segment lower 2624 can expand away from each other by the amount of distance between the overhangs 3008 of the male limiter 3004 and the female limiter 3006 when the implant 2602 of FIG. 26 is in an unexpanded configuration. It is contemplated that the expansion limiters 3002 can be used in combination with the flexible connection 702 of FIG. 7 to provide smooth operation between expanded and unexpanded configurations.

Figure 31:
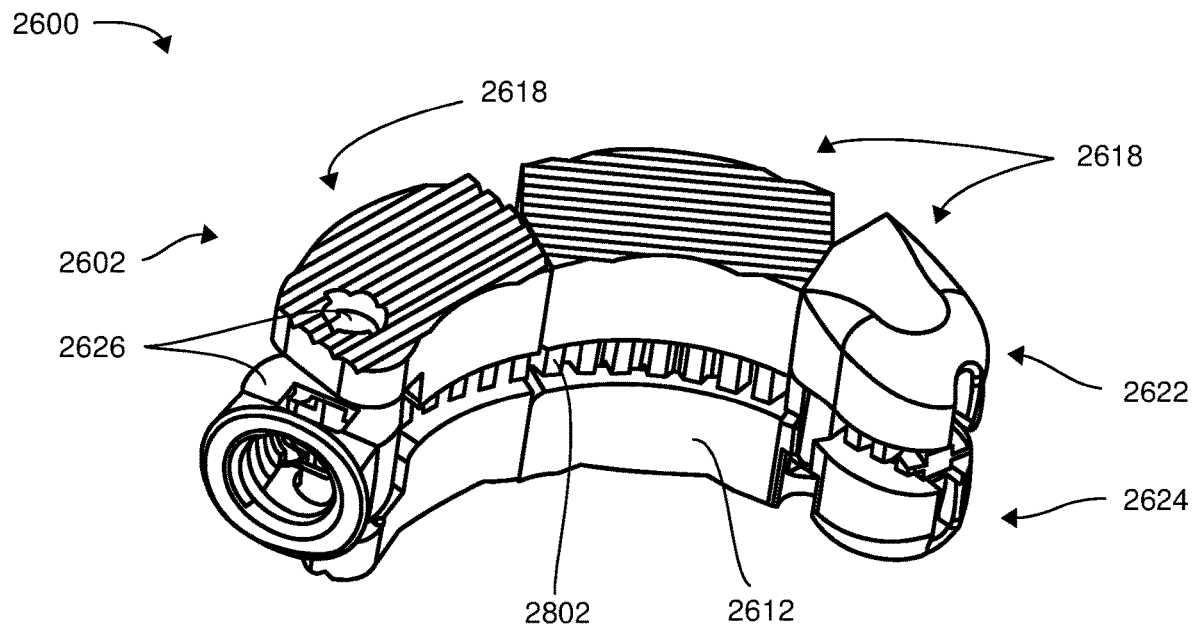
FIG. 31 is an inner isometric view of the fusion system of FIG. 30.

Referring now to FIG. 31, therein is shown an inner isometric view of the fusion system 2600 of FIG. 30. The inner curved surface 2612 of the segment upper 2622 and the segment lower 2624, for each segment 2618, have been moved apart by the expansion mandrel 2802 which has been inserted therebetween. The attachment joint 2626 can be removed ensuring proper dimensions of the implant 2602.

Figure 32:
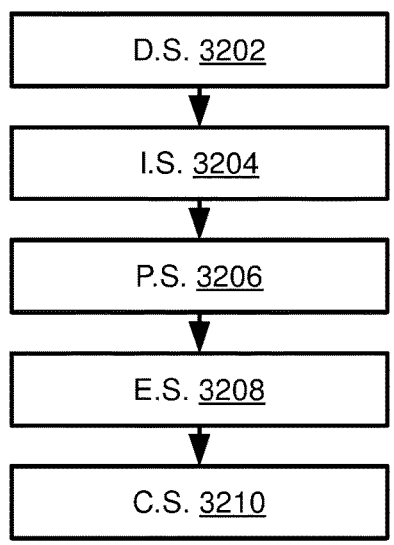
FIG. 32 is a method for operating the fusion system.

Referring now to FIG. 32, therein is shown a method for operating the fusion system. The method can first include performing a discectomy in a discectomy step 3202. After the discectomy step 3202, an insertion step 3204 can be performed.

During the insertion step 3204 the insertion mandrel 128 of FIG. 1 may be retracted thus allowing the implant 102 of FIG. 1 to transition to a non-linear shape. After the insertion step 3204, the implant 102 can be positioned utilizing the insertion mandrel 128. Once the positioning step 3206 is complete, the insertion mandrel 128 can be removed from the delivery tool 104 of FIG. 1 and the implant 102.

After the positioning step 3206, an expansion step 3208 can be performed. During the expansion step 3208 one or more expansion mandrels 704 of FIG. 7 can be inserted into the implant 102, expanding the implant 102 into the expanded configuration.

During insertion of the expansion mandrels in the expansion step 3208, biologics may also be simultaneously injected with a cannulated mandrel or other cannulated implement. After the expansion step 3208, a close step 3210 can be performed. During the close step 3210 the cannulated mandrel can be removed and the access hole closed.

Figure 33:
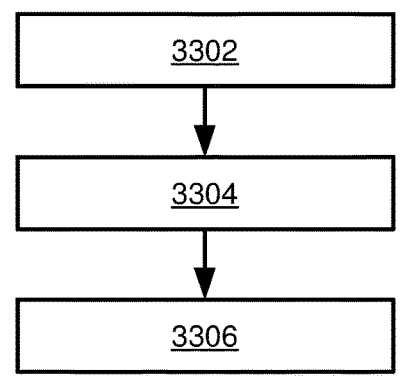
FIG. 33 is a flow chart of a method for manufacturing the fusion system.

Referring now to FIG. 33, therein is shown a flow chart of a method for manufacturing the fusion system. The flow chart can include providing a delivery tool having a shaft and an insertion mandrel in a block 3302; forming an implant pivotally attachable to the delivery tool, the implant having a distal segment coupled to a proximal segment with a flexible guide, the proximal segment having a proximal segment upper and a proximal segment lower, the distal segment having a distal segment upper and a distal segment lower, the implant including: a straight configuration based on the insertion mandrel being extended through the proximal segment and the distal segment, and a curved configuration based on the insertion mandrel being retracted from the distal segment in a block 3304; and forming an expansion mandrel configured for insertion into the implant, the implant including an expanded configuration based on the expansion mandrel being inserted between the proximal segment upper and the proximal segment lower, and being inserted between the distal segment upper and the distal segment lower in a block 3306.

Thus, it has been discovered that the fusion system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the fusion system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. An interbody fusion system comprising:
   a delivery tool having an insertion mandrel;
   an implant having a distal segment coupled to a proximal segment, the proximal segment having a proximal segment upper and a proximal segment lower, the distal segment having a distal segment upper and a distal segment lower, the implant including:
      a straight configuration based on the insertion mandrel being extended through the proximal segment and the distal segment, and
      a curved configuration based on the insertion mandrel being retracted from the distal segment; and
   an expansion mandrel configured for insertion into the implant, the implant including an expanded configuration based on the expansion mandrel being inserted between the proximal segment upper and the proximal segment lower, and being inserted between the distal segment upper and the distal segment lower.

2. The system of claim 1 wherein the expansion mandrel further includes mandrel extensions, the mandrel extensions including non-parallel surfaces for a lordosis adjustment.

3. The system of claim 1 wherein the implant further includes a flexible connection, the flexible connection coupled to the proximal segment upper and the proximal segment lower and providing resistance to expansion between the proximal segment upper and the proximal segment lower.

4. The system of claim 1 wherein the implant further includes an expansion limiter having an overhang, the expansion limiter configured to stop expansion of the implant based on direct contact with the overhang.

5. The system of claim 1 wherein the implant includes a pivoting attachment joint for pivotally coupling the implant to the delivery tool.

6. An interbody fusion system comprising:
   a delivery tool having a shaft and an insertion mandrel;
   an implant pivotally attachable to the delivery tool, the implant having a distal segment coupled to a proximal segment with a flexible guide, the proximal segment having a proximal segment upper and a proximal segment lower, the distal segment having a distal segment upper and a distal segment lower, the implant including:
      a straight configuration based on the insertion mandrel being extended through the proximal segment and the distal segment, and
      a curved configuration based on the insertion mandrel being retracted from the distal segment; and
   an expansion mandrel configured for insertion into the implant, the implant including an expanded configuration based on the expansion mandrel being inserted between the proximal segment upper and the proximal segment lower, and being inserted between the distal segment upper and the distal segment lower.

7. The system of claim 6 wherein the insertion mandrel includes a double-dovetail cross-section for maintaining the implant in an unexpanded configuration.

8. The system of claim 6 wherein the flexible guide includes a curved pre-defined shape.

9. The system of claim 6 wherein the expansion mandrel includes wedges for conforming the expansion mandrel to the curved configuration.

10. The system of claim 6 wherein:
   the insertion mandrel includes a tube cavity;
   the expansion mandrel includes an expansion mandrel inner cavity; and
   the expansion mandrel inner cavity, the tube cavity, or a combination thereof include biologics for introduction into the implant.

11. A method of manufacturing an interbody fusion system comprising:
   providing a delivery tool having an insertion mandrel;
   forming an implant having a distal segment coupled to a proximal segment, the proximal segment having a proximal segment upper and a proximal segment lower, the distal segment having a distal segment upper and a distal segment lower, the implant including:
      a straight configuration based on the insertion mandrel being extended through the proximal segment and the distal segment, and
      a curved configuration based on the insertion mandrel being retracted from the distal segment; and
   forming an expansion mandrel configured for insertion into the implant, the implant including an expanded configuration based on the expansion mandrel being inserted between the proximal segment upper and the proximal segment lower, and being inserted between the distal segment upper and the distal segment lower.

12. The method of claim 11 wherein forming the expansion mandrel further includes forming mandrel extensions, the mandrel extensions including non-parallel surfaces for a lordosis adjustment.

13. The method of claim 11 wherein forming the implant further includes forming a flexible connection, the flexible connection coupled to the proximal segment upper and the proximal segment lower and providing resistance to expansion between the proximal segment upper and the proximal segment lower.

14. The method of claim 11 wherein forming the implant further includes forming an expansion limiter having an overhang, the expansion limiter configured to stop expansion of the implant based on direct contact with the overhang.

15. The method of claim 11 wherein forming the implant includes forming a pivoting attachment joint for pivotally coupling the implant to the delivery tool.

16. The method of claim 11 wherein:
providing the delivery tool includes providing the delivery tool having a shaft;
forming the implant includes forming the implant having the distal segment coupled to the proximal segment with a flexible guide; and
further comprising pivotally coupling the implant to the delivery tool.

17. The method of claim 16 wherein providing the delivery tool includes providing the insertion mandrel with a double-dovetail cross-section for maintaining the implant in an unexpanded configuration.

18. The method of claim 16 wherein forming the implant having the distal segment coupled to the proximal segment with the flexible guide includes forming the flexible guide with a curved pre-defined shape.

19. The method of claim 16 wherein forming the expansion mandrel includes forming wedges for conforming the expansion mandrel to the curved configuration.

20. The method of claim 16 wherein:
providing the delivery tool includes providing the insertion mandrel having a tube cavity;
providing the expansion mandrel includes providing the expansion mandrel having an expansion mandrel inner cavity; and
further comprising introducing biologics into the implant by injecting the biologics into the expansion mandrel inner cavity, the tube cavity, or a combination thereof.

* * * * *